Figure 1:
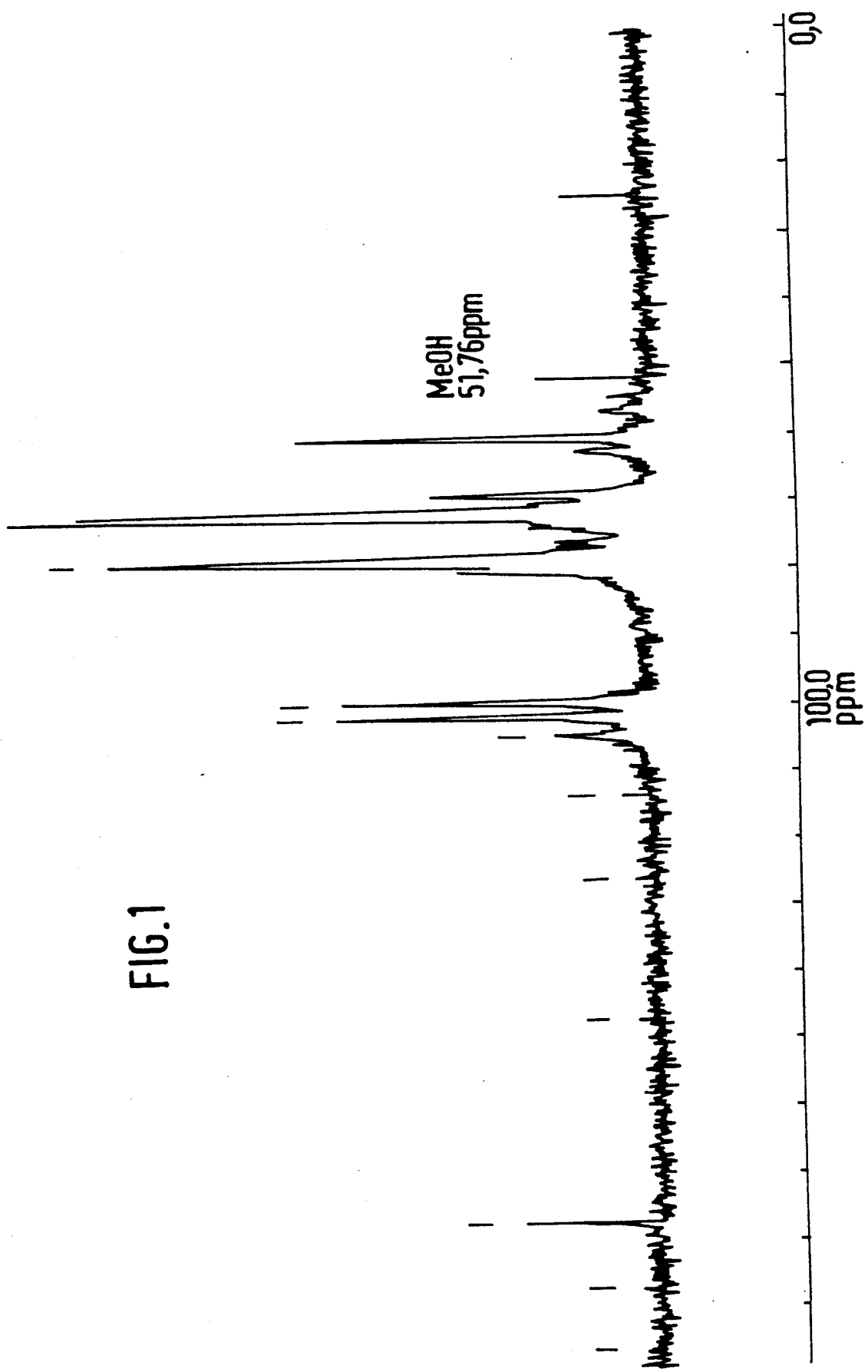

United States Patent [19]

Petitou et al.

[11] Patent Number: 5,013,724

[45] Date of Patent: May 7, 1991

[54] PROCESS FOR THE SULFATION OF GLYCOSAMINOGLYCANS, THE SULFATED GLYCOSAMINOGLYCANS AND THEIR BIOLOGICAL APPLICATIONS

[75] Inventors: Maurice Petitou, Paris Cedex; Jean Choay, Paris, both of France

[73] Assignee: Sanofi Societe Anonyme, Paris, France

[21] Appl. No.: 884,404

[22] Filed: Jul. 11, 1986

[51] Int. Cl.$^5$ ..................... C08B 37/10; A61K 31/725
[52] U.S. Cl. ........................................ 514/54; 514/56; 514/61; 514/53; 514/885; 536/21; 536/55.2; 536/55.3; 536/54; 536/123; 536/124; 536/117; 536/122
[58] Field of Search ....................... 536/21, 55.2, 55.3, 536/54, 123, 124, 122, 119, 18.5; 514/53, 54, 56, 885, 61

[56] References Cited

U.S. PATENT DOCUMENTS

| 3,211,616 | 10/1965 | Yosizawa | 536/54 |
|---|---|---|---|
| 3,247,063 | 4/1966 | Pulver | 514/54 |
| 4,021,544 | 5/1977 | Nair et al. | 514/54 |
| 4,239,754 | 12/1980 | Sache et al. | 514/56 |
| 4,281,108 | 7/1981 | Fussi | 536/21 |
| 4,500,519 | 2/1985 | Lormeau et al. | 514/822 |
| 4,692,435 | 9/1987 | Lormeau et al. | 514/56 |
| 4,692,435 | 9/1987 | Lormeau et al. | 514/56 |
| 4,710,493 | 12/1987 | Landsberger | 514/56 |
| 4,727,063 | 2/1988 | Naggi et al. | 514/822 |

FOREIGN PATENT DOCUMENTS

| 0048860 | 10/1985 | Australia . | |
|---|---|---|---|
| 1180292 | 1/1985 | Canada . | |
| 0011322 | 5/1980 | European Pat. Off. | 514/54 |
| 0040144 | 11/1981 | European Pat. Off. | 536/55.1 |
| 0116251 | 8/1984 | European Pat. Off. | 536/21 |
| 3020220 | 12/1981 | Fed. Rep. of Germany | 536/21 |
| 0136572 | 7/1979 | German Democratic Rep. | 514/54 |
| 0981322 | 12/1982 | U.S.S.R. | 536/21 |
| 2002406 | 8/1978 | United Kingdom . | |

OTHER PUBLICATIONS

Meyer et al., Helvetica Chimica Acta., vol. XXXV, pp. 574–588 (1952), Summary only.

Levy and Petracek, "Chemical and Pharmacological Studies on N-Resulfated Heparin", Proc. Soc. Exp. Biol. Med., vol. 109, pp. 901–905 (1962).

Spencer, "Preparation and Properties of Polysaccharide Sulfates", Disseration Abstracts 21, p. 1747 (1961).

Casu; "Structure and Biological Activity of Heparin", (1985), pp. 51–134, Academic Press, Inc.

Gilbert; Chem. Rev. 62: 549–89 (1962).

Primary Examiner—Ronald W. Griffin
Assistant Examiner—Nancy S. Carson
Attorney, Agent, or Firm—Davis, Hoxie, Faithfull & Hapgood

[57] ABSTRACT

According to the process of the invention, a glycosaminoglycan is used in the form of a salt soluble in an organic medium and is subjected to the action of a given sulfation agent.

69 Claims, 5 Drawing Sheets

PROCESS FOR THE SULFATION OF GLYCOSAMINOGLYCANS, THE SULFATED GLYCOSAMINOGLYCANS AND THEIR BIOLOGICAL APPLICATIONS

The invention relates to a process for the sulfation of glycosaminoglycans.

It also relates to new glycosaminoglycans, or GAGs, exhibiting a variable degree of sulfation, and their biological applications.

In the description which follows and in the claims, the term GAG will be used to refer indiscriminately to a glycosaminoglycan, a fraction of them, a fragment of glycosaminoglycan or one of their pharmacologically acceptable salts.

The expression "degree of sulfation" refers to the number of sulfate groups $OSO_3^-$ per disaccharide unit, uronic acid — amino sugar (or the reverse) or the $SO_3^-/COO^-$ ratio.

It is known that the GAGs are composed, in essence, of alternating residues of a uronic acid and an amino sugar (or the reverse), of the type encountered in the oligo- and polysaccharide chains of biologically active, naturally occurring GAGs such as heparin, heparan sulfate, dermatan sulfate, the chondroitins, the chondroitin sulfates, or hyaluronic acid.

The uronic acid residues are represented, more especially, by D-glucuronic acid or L-iduronic acid, and the amino sugar residues by D-glucosamine or D-galactosamine.

The importance attached to the therapeutic applications of the naturally occurring GAGs mentioned above is known, particularly in the prevention and treatment of disorders of blood coagulation and of diseases associated with disorders of the vascular wall, more especially with thromboses, atheroscleroses and arterioscleroses, or for combatting the ageing of tissues or degenerative symptoms such as alopecia.

It is also known that, by extraction or by chemical or enzymatic depolymerisation of the naturally occurring GAGs, it is possible to prepare GAGs with a lower degree of polymerisation than the naturally occurring substances, endowed, in particular, with a high specific activity towards factor Xa of blood coagulation. By degree of polymerisation (abbreviated to dp), is meant the number of sugar residues, uronic acid or amino sugar in the glycosidic chain.

Depolymerised heparins having a degree of sulfation of at least 2.5, i.e. higher than that of the naturally occurring heparins and of the known, low molecular weight heparins, are described in the application E.0116801 of the 16.12.83 and are offered as medicines with anti-thrombotic, lipid-lowering and fibrinolytic action.

These depolymerised heparins, referred to as hypersulfated heparins in the application EP, are obtained by subjecting a naturally occurring heparin, or a fraction of it, to the action of a mixture of sulfuric acid and chlorosulfonic acid. This acidolytic treatment leads to a mixture of chains with a dp varying from 8 to 30.

The work of the inventors in this field has led them to the observation that, by carrying out a given sulfation treatment under defined conditions, it is possible to change the degree of sulfation of the GAGs in high, usually almost quantitative, yield without impairment to their structure or degree of polymerisation.

In an advantageous manner, the change in the degree of charge of the substances under consideration is found to lead to an improvement in the specificity of their action, in particular, in enhancing some of their properties and diminishing others.

Thus, the aim of the invention is to provide a sulfation process which can give access to defined substances, the degree of charge of which may be altered as desired.

It also relates to the provision of new GAGs of variable charge, in particular to GAGs of defined properties, especially that of a homogeneous degree of polymerisation.

The process according to the invention for the preparation of GAGs of a variable degree of sulfation is characterized in that a given GAG is converted into a salt soluble in an organic solvent, that the salt is dissolved in an organic solvent and in that the salt is treated in solution with a sulfating agent.

These steps can be applied to each GAG and permit the introduction to any desired extent, of sulfate ester groups $OSO_3^-$ instead of primary —OH groups in the sugar residues of the starting GAG without altering its degree of polymerisation or its homogeneity.

The product obtained differs from the starting material only with respect to its different charge and a different distribution of the sulfate groups along the hydrocarbon skeleton. Moreover, its other structural properties are known, in particular, its degree of polymerisation.

Thus, the appropriate choice of the starting GAG is sufficient for the preparation of the desired product.

According to on embodiment of the invention, the starting GAG is composed of alternating residues of D-glucosamine and a uronic acid, namely, L-iduronic acid or D-glucuronic acid. Such sequences are encountered in heparin and heparan sulfate.

In a preferred mode of exploitation, heparin, heparan sulfate, fractions of them or their fragments are used.

In another preferred mode of exploitation, the starting GAG is a GAG of low molecular weight composed of a mixture of chains, or of chains homogeneous with respect to their degree of polymerisation, having a number of sugar residues less than that of heparin or heparan sulfate, in particular, a number of sugar residues varying from 2 to 30.

The low molecular weight (abbreviated as low Mw) GAGs include, in particular, the following substances:

Mucopolysaccharides such as those obtained from heparin by alcoholic extraction, according to patent FR 2 440 376 of the 6.11.1978 and the first certificate of addition 2 461 719 of the 20.07.1979. According to one of the aspects envisaged in the main patent, these products are composed of a mixture of chains of molecular weights between about 2,000 and 8,000, and possessing ratios of Yin Wessler/USP titers of at least 2. Among the substances described, mention will be made of those possessing a YW/USP ratio of the order of 3 to 5 and average molecular weights of 3,000 to 5,500, such as the one referred to hereafter as CY 216.

The process to obtain these comprises:
  suspending in an aqueous alcholic medium of the water-ethanol type, having a titer comprised between about 55° and about 61° GL, preferably of the order of 58° CL, of a substance based on heparin or heparinic constituents whose molecular weights range notably from 2,000 to 50,000, this substance having a low content of inorganic slats, preferably less than 1% by weight.

separating the insoluble fraction and recovering the solution containing the dissolved mucopolysaccharide fraction, from which it can in its turn be separated, notably by alcoholic precipitation, from the above-mentioned aqueous alcohol medium.

The starting material, from which the mucopolysaccharide according to the invention may be extracted may be constituted by a heparin of conventional, injectable pharmaceutical quality, or by a crude heparin such as is obtained at the end of extraction operations for this active principle from tissues or organs of mammals, notably from intestinal mucous or from lugs, for example of pork or beef. It can also be constituted by fractions which are normally discarded (waste) in the purification of such crude heparin, for obtaining a heparin of injectable quality and of higher specific activity, provided of course that the waste materials of lower specific activity still contain heparinic constituents.

It is then possible, from raw material of this type, substantially free from proteins, from nucleic acids and from inorganic salts, preferably when the contents by weight of the latter are less than 1%, to obtain by extraction with 55°–61° GL alcohol a mucopolysaccharide fraction containing constituents of low molecular weight, of which the Yin-Wessler and USP titers are in a ratio of about 2 to about 5, notably from 3 to 5.

It may be remarked that in using water-ethanol mixtures having more than 61' GL, the extraction yield becomes practically zero. On the other hand, the use of aqueous-alcoholic medium of a titer less than 55° CL results in the solubilization of constituents whose presence leads to the lowering of the ratio of the Yin-Wessler/USP titers.

An additional fractionation may be achieved by a supplementary step applied to each mucopolysaccharide fraction, previously redissolved in water, which step consists of adding to this aqueous solution from 1 to 2 volumes of ethanol and from 10 to 100 g/l of sodium chloride and of collecting, on the one hand, the equally active precipitate formed and, on the other hand, the content remaining dissolved in the supernatant liquor, notably by a further alcoholic precipitation and which constitutes a fractionation product whose Yin-Wessler and USP titers respectively are in a ratio still higher, of the order of 6 to 8, than that relating to the initial fraction, notably of the order of 3.

Mucopolysaccharide fractions having a ratio of Yin-Wessler/USP titers which are higher can also be obtained by gel-filtration from the fractions of the first extraction by the 55°–61° GL aqueous-alcohol medium, after prior redissolution of the latter fractions in an aqueous solvent, such as 0.5 M NaCl; 0.1 M tris-HCl solution at pH 7.5. Such a solution may be passed through a gel of polyacrylamide and agarose, in bead form, having the tradename ULTROGEL AcA 44, whose effective fractionating zone is situated between effective molecular weights of 4,000 to 60,000 (for linear molecules).

Mucopolysaccharide fractions of the invention which have a higher Yin-Wessler/USP titer-rations are those which flow after the elution of a volume of 2.5 liters, dead volume not included (the dead volume being the volume of liquid contained in the column of gel, notably in the interstitial spaces between the grains of gel), when the gel-filtration is carried out, with a flow rate of 200 ml/hour, in a column having a diameter of 100 mm and height of 1 m and when the concentration of mucopolysaccharide and the volume of solution placed on the column have been respectively 50 mg/ml and 37.5 ml. The most active fractions are then contained in the 1.5 liters which flow subsequently. The content of the first 2.5 liters is to a great extent formed from heparane-sulphates or heparitine-sulphates, products of high molecular weight and of high viscosity, which do not have anticoagulant activity.

The passage from one column to another column of the same length but of different cross-section entails modification of the volume of solution (of the same concentration) to be placed on the other column, with respect to the volume placed on the preceding column, in a ratio equal to the square of that of the cross-sections (or diameters) of these columns, in order that the same fractions may be obtained in an elution volume from the other column itself also occurring in a ratio with the corresponding elution volume of the preceding column substantially equal to the square of the ratio of said cross-sections.

From fractions having ratio of Yin-Wessler/USP titers of the order of 6 to 8, it is possible to obtain, by additional fractionations, notably by gel filtration or the like, mucopolysaccharide fractions characterized by ratios of Yin-Wessler/USP titers exceeding 10, notably of the order of 13–16, and having Yin-Wessler titers higher than 130, notably 135 to 160 units/mg.

Mucopolysaccharides such as those obtained by limited depolymerisation of heparin by nitrous acid, according, in particular, to the second certificate of addition 2 478 646 of the 20.03.1980 to patent FR 2 440 376 above or the patent application FR 2 503 714 of the 10.04.1981. These substances have the same general characteristics as those mentioned above, but are terminated by residues have the 2,5-anhydro-manno structure.

In particular, mentioned will be made of the mucopolysaccharides possessing a terminal 2,5-anhydro-mannitol residue, such as the one referred to hereafter as CY 222, or a terminal 2,5-anhydro-mannonic acid residue. The molecular weights of the major glycosidic chains are more especially of the order of 2,000 to 3,000, in particular, about 2,000 to 2,600. The ratios of Yin-Wessler/USP titers are, in particular, at least 10, with Yin-Wessler titers of about at least 200 u/mg.

Those compounds of FR 2478646 are formed from a majority of MPS chains endowed with high antithrombotic activity and possessing a ratio of YW/USP titer higher than that of heparin and are subjected to at least one fractionation step, in order to separate selectively those of the MPS chains which possess less than about 6 units. These chains show a ratio of YW to USP titer smaller than those of the starting compositions but higher than those heparin.

Preferably, the fractionation step is carried out by means of a mixture of water containing an inorganic salt and organic solvent, this solvent being selected from among those in which at least a majority of the products sought is selectively insoluble.

The relative proportions of inorganic salt and of solvent are adjusted and this according to the pH of the medium to obtain the desired precipitation.

According to a preferred feature, the organic solvent is advantageously an alcoholic solvent, more especially ethanol.

According to another preferred feature, the organic salt used is constituted, particularly, by the sodium or potassium chloride or any other salt miscible in the organic solvent used.

According to another preferred feature, the pH of the reaction mixture is adjusted to a value corresponding to an acid pH, more especially to a pH less than 4.

According to the preferred embodiment, the MPS compositions employed for the fractionation possess a ratio of the YW to USP titers of at least about 10 and a YW titer of about 200 to 250 u/mg.

The fractionation is carried out by means of an organic solvent enabling the selective precipitation of the MPS possessing the highest molecular weights and consequently, a ratio of the YW to USP titers less than 10, particularly less than 6, preferably less than 5, and more especially in the vicinity of 4.

Preferably, the organic solvent is an alcoholic-solvent, more especially ethanol.

The employment of the features which follow enables the production satisfactorily more especially of MPS possessing a ratio of the YW to USP titers below 10, preferably of about 6 to 3, more especially of the order of 4 and YW titer higher than that of heparin and at least about 180 to 200 u/mg.

The MPS compositions corresponding to the characteristics of YW and USP titers given above are placed in solution in a proportion of 5% w/v in water containing 10 g/l of NaCl.

After adjustment of the pH to 3.8, the fractionation of these MPS is carried out by means of one volume of ethanol. The precipitate formed which contains the desired products is then recovered.

Preferably, the MPS compositions employed possess at the reducing end, a unit of 2,5 anhydromanno structure, preferably selected from among 2,5 anhydromanno, 2,5-anhydromannitol or 2,5 anhydromannonic acid groups.

These compositions are advantageously obtained by a partial depolymerisation process of heparin under the action of chemical agents such a nitrous acid.

The MPS compositions recovered on precipitation are characterised in that they are essentially formed of chains (1) of an average molecular weight of 3000 to 6000 daltons, particularly from 4000 to 5000, (2) possessing a YW titer of about at least 180 to 200 u/mg and a ratio of the YW/USP titer, less than 10, particularly of about 6 to 3, (3) terminated by units of 2,5-anhydromanno structure.

According to the method of FR 2,503,714, biologically active mucopolysaccharides, or MPS, of high purity are produced by controlled depolymerisation of heparin, which comprises reacting heparin and nitrous acid in an aqueous medium at a pH of 2 to 3, in quantities such that the heparin concentration is at least 80% by weight and the molarity of the nitrous acid is 0.02 to 0.1 M, these data being calculated with respect to the total quantity of the mixture of reactants used, and after the depolymerization reaction has stopped of its own accord by exhaustion of the nitrous acid, the mixture of MPS, which can be precipitated by an alcoholic solvent, is recovered. The pH of the aqueous medium is about 2.5.

Mucopolysaccharides composed essentially of chains (1) of average molecular weight of from 3,000 to 6,000, in particular, of about 4,000 to 5,000 (2), possessing a YW/USP ratio of less than 10, in particular of about 6 to 3 (3), and terminated by residues of the 2,5-anhydromanno structure, such as those obtained, for example, according to the patent application FR 2 572 080 of the 18.10.1984.

To obtain these, a fractionation step is carried out by means of a mixture of water containing an inorganic salt and organic solvent, this solvent being selected from among those in which at least a majority of the products sought is selectively insoluble and precipitates.

The relative proportions of inorganic salt and of solvent are adjusted and this according to the pH of the medium to obtain the desired precipitation of the MPS chains.

According to a preferred feature the organic solvent is advantageously an alcholic solvent, more especially ethanol.

According to another preferred feature, the organic salt used is constituted, particularly, by the sodium or potassium chloride or any other salt miscible in the organic solvent used.

According to another preferred feature, the pH of the reaction mixture is adjusted to a value corresponding to an acid pH, more especially to a pH less than 4. According to a preferred embodiment of the invention, the MPS compositions employed for the fractionation contain a majority of chains of MW in the range of about 1800 to 8000, possessing a ratio of the YW to USP titers of at least about 10 and YW titer of about 200 to 250 u/mg.

The YIN-Wessler titer is used for measuring the anti XA activity according to YIN et al in J. Lab. Clin. Med 1973, 81, P. 298.

These compositions are advantageously obtained by a partial depolymerisation process of heparin under the action of chemical agents such as nitrous acid. Recourse is had particularly to the process described by Applicants in the second application for a certificate of addition No. 8006282 of 20.03.1980 to patent FR 7831357 of 6.11.1978. Advantageously, the depolymerisation process which is performed is based on self-regulation of the depolymerisation reaction such as described in patent application FR 8107283 of 10.04.1981 in the name of Applicants.

According to the most general aspect of this autoregulated depolymerisation, heparin is reacted with nitrous acid in an aqueous medium at a pH of about 2 to 3, advantageously of 2.5, in amounts such that heparin concentration is of at least about 8% in weight an nitrous acid molarity of about 0.02 M to 0.1 M.

When the depolymerisation reactions stops by itself, after having consumed all the nitrous acid, the MPS mixture of the kind of those which can be precipitated by an organic solvent is recovered.

Nitrous acid is generated in situ by adding an acid having advantageously biologically acceptable anions, such as HCl or $CH_3COOH$, to a nitrous acid derivative, particularly, a salt, an ether-salt and more especially an alkaline or an alkaline-earth salt. $NaNO_2$ is more particularly used at a molarity of 0.03 to 0.5 M.

The process is preferably performed with a $NaNO_2$ molarity of 0.040 M to 0.046 M more particularly of about 0.043 M.

Preferably, the MPS compositions employed possess at the reducing end, a unit of 2,5 anhydromanno structure, preferably selected from among 2,5-anhydromannonic acid groups.

The starting MPS compositions corresponding to the characteristics of YW and USP titers given above are placed n solution in a proportion of 5% w/v in water containing 10 g/l of NaCl.

After adjustment of the pH to 3.8, the fractionation of these MPS is carried out by means of an organic solvent enabling the selective precipitation of the MPS chains possessing the highest molecular weights and/or the most sulfated of the mixture chains.

Preferably the organic solvent is an alcoholic solvent, more especially ethanol.

The elimination of low NW chains of the low sulfate content chains results in fractions of a higher USP titer, the YW titer being practically maintained.

The MPS compositions recovered on precipitation are characterized in that they are essentially formed of chains (1) of an average molecular weight of 4000 to 5000 daltons, particularly about 4500 (2) possessing a YW titer of about 180 to 200 u/mg and a ratio of the YW/USP titers, less than 10, particularly of about 6 to 3 more especially of about 4. Said compositions are formed of a majority of chains which are terminated by units of 2.5-anhydromanno structure when the starting compositions are obtained by a nitrous heparin depolymerisation process.

Oligosaccharides composed of maximally 8 sugar residues, with a high Yin-Wessler titer which may rise to 2,000 u/mg and a low USP titer, almost zero, endowed with a high affinity for AT-III, such as those described, in particular, in the application EP 0027089 of the 6.10.1980.

According to one variant, these oligosaccharides are obtained by limited nitrous acid depolymerisation and are terminated by residues of the 2,5-anhydro-manno structure.

According to another variant, the residue at the beginning of the chain corresponds to an unsaturated uronic acid residue, such as that formed by subjecting heparin to a limited depolymerisation with heparinase. In particular, these oligosaccharides are composed of octasaccharides of the structure ABCDEFGH, corresponding to the formula below:

including a sequence consisting of less than 8 moieties which sequence is responsible, to a large extent, for the specific anti-Xa activity of the products;

treating the depolymerization mixture to separate at least the major part of the above defined oligosaccharidic chains said treatment advantageously comprising (a) the contact of the depolymerization mixture with AT III for selecting at least the major part, advantageously practically the totality of the oligosaccharides possessing a sequence having the specific structure necessary to recognize and bind AT III, (b) the elimination of the unselected products, (c) the recovering of the selected products. Said oligosaccharides can be characterized by the fact they possess a specific structure capable of binding AT III. They have an anti-Xa activity higher than heparin and a very low global anticoagulant activity.

The products having an AT III affinity as recovered from the above mentioned process, are submitted to one or several steps in order to selectively separate the above-defined oligosaccharides having short chains. The process for obtaining these fractions comprises heparin depolymerization and the treatment of the resulting depolymerization mixture so as to separate the fractions containing oligosaccharides having no more than 8 saccharidic moieties (advantageously the oligosaccharides per se) having a high AT III affinity and a high anti-Xa (Yin-Wessler) activity.

The depolymerization step is carried out under mild conditions so that the oligosaccaharidic chains are not completely degraded and the moieties which are responsible (to a large extent) for anti-Xa (Yin-Wessler) activity are maintained.

Preferably, the depolymerizing conditions of the process defined hereabove are so adjusted as to maintain the capability of at least a part of the resulting oligosac-

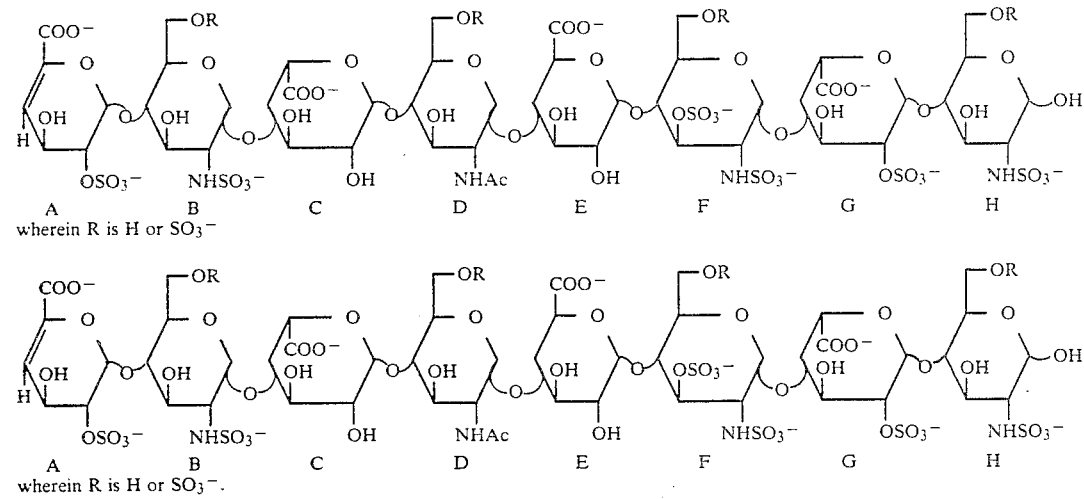

The oligosaccharides of EP 027089 are of the type obtainable by a process which comprises the steps of
contacting heparin (or heparinic fractions) possessing anticoagulant activity and having chains with molecular weights ranging from about 2000 to about 50000, with an agent capable of depolymerizing or fragmenting the heparinic chains, the conditions used for carrying out that step being adjusted so as to obtain a depolymerization mixture which contains oligosaccharidic fragments or chains, constituted by no more than 8 moieties yet having an anti-Xa Yin-Wessler activity and charides of being specifically retained on immobilized antithrombin III.

The above adjustment can also advantageously be based on the upkeeping of the capability of at least part of the resulting oligosaccharides to exhibit anti-Xa activity as measurable by the Yin-Wessler test, while having practically no more anticoagulant activity as measured by the USP test.

It will be appreciated that the threshold with respect to the adjustment of the depolymerization conditions need not necessarily be attained. It is nevertheless desirable not to do so when high yields of oligosaccharides having Yin-Wessler anti-Xa activity are desired.

When depolymerizing heparin with $HNO_2$, it seems advantageous to carry out the reaction in aqueous medium, at a pH ranging from 2 to 4, preferably 2 and at a temperature close to ambient.

When depolymerization with heparinase, a highly purified heparinase should preferably be used, in particular a bacterial heparinase, more especially originating from Flavorbacterium heparinum. The conditions are controlled in order to obtain the smallest fragments still having an affinity for AT III and an anti Xa (Yin-Wessler) activity.

It is advantageously carried out at a pH ranging from 6 to 8, in particular close to neutral and at a temperature close to ambient. The heparinase in gradually added in the reaction mixture until hydrolysis is over.

The depolymerization with the heparinase my be optionally carried out on the fractions resulting from the oligosaccharidic factions obtained after degradation of heparin with $HNO_2$, or also on the oligosaccharides of higher molecular weight which are retained on immobilized AT III together with the active oligosaccharides having less than 8 moieties and which are then eluted with these oligosaccharides having shorter chains.

The separation and the recovery of the fractions which contain the desired oligosaccharides is advantageously carried out by affinity chromatography in a column containing bound AT III.

Satisfactory results are obtained by using a gel of agarose such as the one commercialized under the trademark Sepharose, with AT III molecules linked thereon.

To achieve the desired separation of the major part of the products contained in the depolymerization mixture and having a high anti-Xa activity, the column is advantageously equilibrated with a buffer having an ionic strength of about 0.2 M, preferably not less than 400.1 M at a pH of 6 to 8, preferably close to or slightly higher than neutral.

The products devoid of or having a low affinity for AT III are eliminated by rinsing with a buffer advantageously of the same type as the one used for equilibrating the column.

A preferred embodiment for recovering the AT III retained or absorbed products having an anti-Xa activity (Yin-Wessler) comprises desorbing and recovering all of the oligosaccharides by eluting them with a buffer having a sufficient ionic strength to that effect. The buffer used for the above mentioned elution is further advantageously selected among those which do not interfere with the subsequent recovery steps (particulary with alcohol precipitation) of the oligosaccharide contained in the reconvened fractions. A buffer containing a calcium salt, such as calcium chloride that remains soluble in presence of an alcohol concentration (any suitable alcohol, for instance ethanol) which causes the precipitation of the oligosaccharides is thus preferred.

A sodium salt can also be used.

After elution of the products having an AT III affinity, an alcoholic precipitation is advantageously carried out to recover them, their separation being then made for example by centrifugation.

In order to have oligosaccharide fractions having the required high anti-Xa activity (Yin-Wessler) and a satisfactory homogeneity, the mixture of all the oligosaccharides previously retained on AT III is fractionated by a gel filtration or by ion exchange chromatography or both or by any other method which would yield similar results.

Homogeneous mixtures of hexasaccharides, such as those obtained according to application FR 2 504 928 of the 29.04.1981, by subjecting the above octasaccharides to limited digestion by a heparinase. In particular, these mixtures correspond to the formula below:

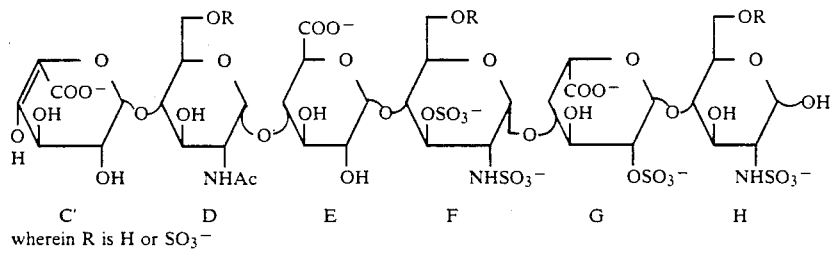

wherein R is H or $SO_3^-$

To obtain the hexasaccharides, the octasaccharides are contacted with an enzymatic agent under conditions adjusted so as to fragment these octasaccharides specifically in order to eliminate A-B units, the fragmentation resulting in chains essentially formed of hexassacharides possessing the sequence denoted by the abbreviation C-H. Advantageously heparinase is used as enzyme. Said heparinase is of bacterial origin and obtainable from Flavobacterium heparinum. The heparinase applied possesses a heparinasic activity of about 90 000 units (the determination being effected with a heparin titrating at least 215 iu/mg at 230 nm), this enzyme being applied at concentrations of the order of 0.25 to 1 mg per mg of octasaccharides treated, preferably of the order of 0.5 mg of enzymes per mg of octasaccharides. To provide hexasaccharide compositions highly homogeneous in C'-H hexasaccharides, the mixture resulting from the enzymatic reaction is subjected to fractionation, for example, by gel permeation according to the molecular weight and/or the ionic density of the product.

Oligo- or polysaccharides, homogeneous with respect to degree of polymerisation, in particular, those obtained by filtration through a material such as Sephadex or by chromatography employing an ionic strength gradient of the substances CY 222, CY 216, heparin or other GAGs.

GAGs such as those obtained by the action of periodate on heparin, followed by treatment in basic medium.

GAGs, homogeneous with respect to their degree of polymerisation, such as those obtained, for example, by gel filtration of a mixture resulting from the depolymerisation of heparin.

GAGs such as those obtained by the depolymerisation of heparin by heparinase or nitrous acid, the separation of the fractions possessing the sequence which binds to AT-III and the gel filtration of these fractions in order to obtain fragments of GAGs exhibiting varying degrees of polymerisation and having an affinity for AT-III.

These could be, for example, fragments with a degree of polymerisation higher than 12, on the one hand, and on the other, of GAG fragments having a lower degree of polymerisation, in particular, a dp of 12, 10, 8, 6, 4 and 2 sugar residues.

The GAGs such as those mentioned above, but almost totally lacking the sequence able to specifically recognize AT-III and with YW titers varying from low to zero. In particular, these are oligosaccharides which do not bind to AT-III in the procedures including a step in which heparin or GAGs are mixed with AT-III, followed by gel filtration to separate the oligosaccharides of various dps into homogeneous fragments.

The GAG fractions and fragments of GAGs mentioned above possessing chain sequences such as those encountered in heparin, in which some, even the majority and possibly all of the —NHSO$_3$⁻ groups in position 2 of the glucosamine residues are replaced by -NH-acyl groups, in particular, by —NH—acetyl groups, or by —NH$_2$ groups.

So-called total GAGs, corresponding to mixtures of GAGs obtained by treatment of animal organs.

These different GAGs are only mentioned by way of examples, it being understood that they correspond to substances especially well known to the Applicant who developed them and has described them in the various patents and patent applications mentioned above, and filed in her name.

However, as already indicated, the procedure of the invention has the advantage of being able to make use of any type of GAG.

Thus, according to another embodiment of the invention, the GAG used is composed of alternating residues of D-galactosamine and a uronic acid. In a preferred mode of the exploitation, the starting GAG is chosen from among dermatan sulfate, the chondroitins, the chondroitin sulfates or hyaluronic acid, fractions of them or their fragments.

In one variant, dermatan sulfate is used.

According to one provision of the invention, one or several primary or secondary —OH groups of the sugar residues of the above GAGs are masked by protecting groups, a circumstance which allows other positions to be sulfated as desired, after which the protecting groups may be removed to regenerate the free —OH groups.

Such protecting groups are chosen from among acyl groups such as acetyl, substituted acetyl, benzoyl.

The GAG salt subjected to the sulfation reaction is a salt soluble in an organic solvent.

It is preferably an amine salt.

As amine component, use is advantageously made of an amine of the formula —N(R$_1$, R$_2$, R$_3$) in which R$_1$, R$_2$ and/or R$_3$ represent a hydrogen atom or an aliphatic chain of from 1 to 10 carbon atoms, in particular, triethylamine or tributylamine or a quaternary ammonium salt such as tetraethylammonium or tetrabutyl ammonium or benzethonium.

It is clear that the nature of the salt can influence the sulfation reaction by virtue, for example, of the steric hindrance it affords, a consequence of which could be the preferred sulfation of certain positions.

The GAG salt is advantageously prepared by treating the GAG in its acid form, obtained by chromatography on a cation exchange resin, with the amine corresponding to the desired salt.

The GAG salt i dissolved in an organic solvent. More especially, a dipolar aprotic solvent such as dimethylformamide (DMF), dimethylsulfoxide (DMSO), hexamethylphosphotriamide (HMPT) or acetonitrile is used. Pyridine is another possibility.

In an advantageous manner, the sulfating agent is chosen from among a complex of sulfur trioxide with an organic base such as trimethylamine (TMA) or pyridine, or chlorosulfonic acid in pyridine.

Equivalent sulfating agents are described by E. E. Gilbert in Chemical Reviews 1962, vol. 62, 549–589.

Study of the reaction conditions shows that a satisfactory degree of sulfation is obtained by using about 1 to 5 equivalents of complex per —OH group of the GAG.

The sulfation reaction is advantageously carried out at a temperature between 0° C. and 100° C., in particular, at about ambient temperature or above, for about 10 to 14 hours. In some cases, temperatures lower than the ambient temperature, i.e. 20° C., may be used.

The reaction conditions, in particular, reaction solvent, time and temperature are chosen so as to be able to carry out selective reactions.

Any protecting groups which may be present are removed by saponification in the case of O-acyl protection, in particular O-acetyl, and by hydrogenolysis in the presence of a catalyst in the case of a benzoyl group.

The product is recovered from the reaction mixture by either a gel filtration step or an ultrafiltration step, followed by conversion to the desired cationic form by means of a cation exchange resin. The product is then precipitated by a solvent miscible with water or lyophilised.

According to one variant, the hypersulfated GAG obtained is subjected to gel filtration in order to obtain GAGs which are homogeneous with respect to their degree of polymerisation.

The techniques which make use of nitrous acid, heparinase or periodate give rise to chains with an even dp.

The foregoing steps lead to controlled sulfation with respect to the desired degree of sulfation, with a high yield of defined products without degradation of their glycosidic structure nor loss of homogeneity.

It will also be noted that the sulfation procedure of the invention, which does not cause changes in the structure of the starting material, makes available GAGs of a variable degree of sulfation and homogeneous with respect to their dp if one additional separation step is carried out before or after sulfation.

Thus, it is possible to prepare directly the product which is appropriate for a particular application.

The GAGs according to the invention with an altered sulfation pattern, homogeneous with respect to their degree of polymerisation, or as mixtures, are characterised in that they can be represented by the following formula I:

$$R-(XY)_n-R' \quad (I)$$

in which:
- R represents a uronic acid or an unsaturated uronic acid or an OH group.
- X represents a glucosamine or a galactosamine moiety in which the carbon atom at position 2 is substituted by a $NHSO_3^-$ group, or, in the case of glucosamine and chains of the heparin type, by an $NH_2$ or NH-acyl group.
- Y represents a uronic acid, namely D-glucuronic acid or L-iduronic acid.
- n is an integer between 0 and 80.
- R' represents a glucosamine or galactosamine moiety in which the carbon atom at position 2 is substituted by a $NHSO_3^-$ group, or, in the case o glucosamine and chains of the heparin type, by an $NH_2$ or NH-acyl group, or represents an —OH group or a glucosamine residue rearranged to a grouping with a 2,5-anhydromanno structure, or a galactosamine residue rearranged to a group with a 2,5-anhydrohexitol structure.

the primary and secondary OH groups of the residues X and Y and, if the case arises, of R and R', being sulfated, such as the position and/or number of sulfate groups in the chain of the GAGs being different from those encountered in the naturally occurring chains or the depolymerised derivatives of these naturally occurring GAGs, or their pharmacologically acceptable salts, excluding mixtures of chains with non-modified termini having a total number of glucosamine and uronic acid residues of from 8 to 30.

A preferred family of substances corresponds to the formula II:

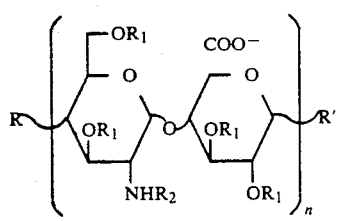

in which:
- $R_1$ represents H or $SO_3^-$
- $R_2$ represents H, $SO_3^-$ or an acyl group, in particular acetyl,
- R and R' have the meanings given above.

In another preferred family, X and possibly R' represent a galactosamine residue, the linkage between the galactosamine and uronic acid residues being of the 1→4β D type and those between the uronic acid and the galactosamine residues possibly present being of the type 1→3 α L or 1→3 β D.

A preferred group of these families consists of the GAGs which contain a number of sugar residues less than or equal to 12.

In particular, these are GAGs in which R represents an unsaturated uronic acid residue.

As a variant, these are GAGs in which R' represents a group with the 2,5-anhydromanno structure when the rearranged residue is a glucosamine moiety or with the 2,5-anhydrohexitol structure when the rearranged residue is a galactosamine moiety. In preferred GAGs, 7 R' represents a group with the 2,5-anhydromannitol structure.

Advantageous GAGs of this preferred group consists of a mixture of GAGs or GAGs homogeneous with respect to their degree of polymerisation, the chains having four, six or eight sugar residues.

In these GAGs, R and R' either both represent an OH or are respectively a uronic acid and a glucosamine residue, or R' represents a group with the 2,5-anhydromanno structure, preferably a group with the 2,5-anhydromannitol structure.

Other advantageous GAGs consist of mixtures of chains of dp 8, 10 and 12 in which R and/or R' represent a modified sugar residue.

Other advantageous GAGs consist of GAGs which are homogeneous with respect to their degree of polymerisation, the chains possessing eight, ten or twelve sugar residues.

Still other GAGs consist of a mixture of chains represented by the formula I in which n is an integer between 3 and 15, and R and/or R' represent a modified sugar residue.

According to one variant, the carbon atom in position 2 of the glucosamine moiety is substituted by an $NH_2$ or NH-acyl group, in particular NH-acetyl.

Such GAGs are advantageously prepared from starting materials consisting of mucopolysaccharides such as those obtained by limited depolymerisation with nitrous acid, composed of a mixture of chains with a terminal 2,5-anhydromanno residue, in particular, a 2,5-anhydromannitol, of molecular weight of about 2,000 to 8,000, possessing a ratio of YW/USP titers of at least 10, a Yin-Wessler titer of at least 200 μ/mg and average molecular weights of 2,000 to 3,000.

As a variant, these GAGs are prepared from starting materials consisting of mucopolysaccharides such as those obtained by careful depolymerisation with nitrous acid, and are composed of a mixture of chains having a terminal 2,5-anhydromanno residue, in particular, 2,5-anhydromannitol, possessing a ratio of Yin-Wessler-/USP titers of about 3 to 6 and average molecular weights of 4,000 to 5,000.

Another preferred group of families with alternating residues of glucosamine and a uronic acid or galactosamine and a uronic acid or the reverse contains a number of sugar residues higher than 30.

In an advantageous manner, the GAGs obtained according to the invention make it possible to modulate a given biological property in a specific manner.

Such properties in which biological activity is modulated as a function of the change in the sulfation pattern have been verified in several model systems.

ACTIVITY ON BLOOD COAGULATION (a) inhibitory activity towards the activated factor X (factor Xa). In this study the determination is carried out using a chromogenic substrate S 2222 (Kabi, Stockholm), according to the method described by Teien and Lie, Thrombos. Res., 1977, 10. 3:399–410.

The result is expressed in units per mg of product tested.

(b) inhibitory activity towards the activated factor II (factor IIa) or thrombin. In this model, the concentration of glycosaminoglycan capable of bringing about 50 % inhibition of the activity of factor IIa in the presence of antithrombin III (AT-III) or cofactor II of heparin (HC II) is determined.

The results are expressed in µg of product per ml.

(c) measurement of the coagulation time by the APTT method (as described in Caen, J., Larrieu, M. J., and Samama, in Hemostase, paris, Expansion Scientifique Francaise, 1968, pp 133–135).

In the present instance, the concentration of the product to be tested necessary for a doubling of the coagulation time is determined.

The result is expressed in µg of substance tested per ml.

(d) anti-thrombotic activity in vivo in the rabbit, according to the model of Wessler (such as that described by Wessler, S., Reimer, S. M. and Sheps, M. C., in J. Appl. Physiol. 14 (6), 943–946, 1959).

The test substance is injected into the carotid artery, at doses varying from 10 to 500 µg/kg, 3 mn before the administration of the thrombogenic agent (human thromboplastin).

The result is expressed as percentage of inhibition of thrombus formation.

STUDY OF THE BINDING TO ENDOTHELIAL CELLS

Experimental system

Cell cultures primary cultures of endothelial cells of the human umbilical vein, prepared according to the technique of Jaffe et al., are cultured in M 199 medium to which 20 % fetal calf serum (FCS) has been added, in a humid atmosphere containing 5 % of $CO_2$.

Between the 5th and the 6th day monolayers of confluent cells are obtained.

Experiment demonstration of binding to endothelial cells 24 hours before each assay the medium containing the FCS is removed and the cells are washed with a medium containing 2 % of Ultroser. Incubation with the labelled heparins is preformed in 2 ml of medium. After incubation, the cells are washed three times with 1.5 ml of phosphate buffer (PBS, pH 7.4), then they are detached and solubilized by incubation with 0.5 ml of pronase (1 mg/ml) and 0.1 % (v/v) of Triton X 100 for 30 mn at 37.C.

The radioactivity of the cells and of the incubation medium are measured by means of a gamma counter Beckmann 7000 ($^{125}I$)

Competition experiment with a sample of $^{125}I$-labelled heparin

The cells were incubated for 5 hours with a low concentration of $^{125}I$-heparin in the presence of different concentrations of unlabelled test substances (heparin control, hypersulfated heparin, etc. . . ).

The capacity to inhibit the binding of heparin was expressed as an $I_{50}$ (concentration which brings about 50 % inhibition of the binding of the labelled heparin).

This value indicates the affinity of the best substances for endothelial cells.

INHIBITORY ACTIVITY TOWARDS COMPLEMENT

Heparin inhibits the formation of the $C_3$ convertase, amplifier of the alternative complement activation pathway, by inhibiting the formation of the bimolecular complex between the proteins $C_{3b}$ and B.

The effect of heparin and its derivatives on the binding of $C_{3b}$ to B was studied by using protein B labelled with $^{125}I$ ($^{125}I$-B) and sheep erythrocytes as carriers of protein $C_{3b}$ ($E^SC_{3b}$).

The $IC_{50}$ is the concentration of heparin oligosaccharide in the assay necessary to cause 50 % inhibition of the formation of the complex $C_{3b}$-B.

This measurement is performed in vitro, in a system using purified proteins.

Experimental system $E^SC_{3b}$ (0.75–2.5 × 10$^7$) are incubated with different concentrations of $^{125}I$-B in veronal buffer containing 0.1 % gelatin and 5 mM $Mg^{2+}$ for 30 mn at 30° C.

70 µl aliquots are taken in duplicate from each reaction mixture and added to 300 µl of a mixture of dibutylphthalate (Merck-Clevenot, France) and dinonylphthalate (Coger, paris) (7:3 v/v) in 0.5 ml poly propylene tubes The tube are Centrifuged for one mn at 8,000 ×g in a Beckmann microfuge (Beckmann, paris), then cut just above the precipitates. The radioactivity of the bound ligand is counted.

ACTIVITY TOWARDS ELASTASE AND CATHEPSIN G

Experimental system

Leucocyte elastase is prepared from rat polymorphonuclear leucocyte derived from a pleural exudate. The substrate used is N-succinyltrialanyl paranitroanilide and enzymatic activity is determined after pre-incubation of the enzyme with the test substance for 2 hours at ambient temperature (20° C.). The substrate is then added, the mixture is incubated for 20 hours at 37° C. and the optical density is read at 410 nm.

The determination of human cathepsin G, obtained from human polymorphonuclear leucocytes, is performed using azocasein as substrate. In this case, too, the enzyme is pre-incubated with the test substance at ambient temperature for 1 hour. Azocasein is then added and the mixture is incubated for 5 hours at 37° C. precipitation is carried out with trichloracetic acid to give a final TCA concentration of 5 %, the mixture is centrifuged and the optical density is read at 366 nm.

Five series of experiments were carried out.

EXPERIMENT 1
STUDY OF THE ANTICOAGULANT ACTIVITY OF HYPERSULFATED HEPARIN AND DERMATAN SULFATE (A) Inhibition of factors Xa and IIa in the presence of AT-III or HC II

| SUBSTANCE TESTED | Chromogenic anti-Xa activity $\mu$/mg | Anti-IIa activity | |
|---|---|---|---|
| | | AT-III IC 50 $\mu$g/ml | HC II |
| Normal heparin | 192 | 0.10 | 0.29 |
| Sursulfated heparin IC 84 1545 | 79 | 0.037 | 0.045 |
| Sursulfated N-desulfated N-acetylated heparin IC 86 1746 | 2 | 0.38 | 0.077 |
| Dermatan sulfate | — | 100 | 5.8 |
| Sursulfated dermatan sulfate IC 85 1610 | — | 17 | 0.34 |

It can be seen that the anti-thrombin activity (anti-IIa) increases with the degree of sulfation.

In the case of hypersulfated N-acetylated heparin, the activity manifested in the presence of HC II is increased with respect to that of the starting heparin (IC 50 changing from 0.29 to 0.077), whereas the activity shown in the presence of AT-III is diminished (IC 50 changes from 0.10 to 0.38).

(B) Measurement of the coagulation time by the APTT method

| SUBSTANCE TESTED | Concentration necessary to double the coagulation time - $\mu$g/ml |
|---|---|
| Normal heparin | 1.8 |
| Sursulfated heparin IC 84 1545 | 4.5 |
| Dermatan sulfate | 50 |
| Sursulfated dermatan sulfate IC 85 1610 | 15 |

It can be seen that, in this model system, sursulfated heparin is less active than normal heparin, whereas sursulfation increases the activity of dermatan sulfate.

Additional experiments in plasma have shown that the action of normal heparin is dependent upon AT-III, whereas the action of sursulfated heparin is independent of cofactors.

These experiments have also shown that the action of normal dermatan sulfate is totally dependent on HC 11, whereas that of sursulfated dermatan sulfate is only partially dependent on it.

(C) Antithrombotic activity of dermatan sulfate and sulsulfated dermatan sulfate in vivo in the rabbit The results obtained in the Wessler model which makes use of human thromboplastin as thrombogenic agent, showed that, at a dose of 100 $\mu$g/kg, the prevention of thrombus formation was of the order of 80 % for sursulfated dermatan sulfate, but only 40 % for dermatan sulfate at the same dose.

EXPERIMENT 2
STUDY OF THE ANTICOAGULANT ACTIVITY OF SURSULFATED HEPARIN FRAGMENTS, HOMOGENEOUS WITH RESPECT TO THEIR DEGREE OF POLYMERISATION (dp)

In this model system, the inhibition of factor IIa is determined by measuring the IC 50 of the test substances in the presence of AT-III and HC II.

The following substances were tested : reference sample of heparin and heparin fragments having degrees of polymerisation equal to 4 (dp 4), 6 (dp 6), 8 (dp 8), 12 (dp 12) and 16 (dp 16), as well as their sursulfated homologues.

| SUBSTANCE TESTED | Anti-IIa activity | |
|---|---|---|
| | AT III IC 50 $\mu$g/ml | HC II |
| Heparin standard | 0.039 | 0.14 |
| IC 84 1477 dp 4 | 100 | — |
| IC 85 1597 dp 4 sursulfated | 100 | — |
| IC 84 1476 dp 6 | 100 | — |
| IC 85 1598 dp 6 sursulfated | 100 | 42 |
| IC 84 1475 dp 8 | 100 | — |
| IC 85 1599 dp 8 sursulfated | 100 | 11 |
| IC 85 1473 dp 12 | 100 | 56 |
| IC 85 1600 dp 12 sursulfated | 100 | 3.6 |
| IC 84 1552 dp 16 | 100 | 22 |
| IC 85 1601 dp 16 sursulfated | — | 0.68 |

=50 % not attained. In contrast with heparin, it can be seen that the homogeneous fragments of low molecular weight exhibit no anti-IIa activity in the presence of AT-III in this system before sursulfation, since the IC 50 is higher than 100.

The sursulfation of these fragments does not lead to any change in activity in the presence of AT-III, with the exception of dp 16, which acquires slight activity on sursulfation.

In contrast, anti-IIa activity in the presence of HC II is increased by sursulfation, in particular, it increases as the molecular weight.

Nonetheless, the anti-IIa activity in the presence of HC II remains low compared with that of heparin (with the exception of fragment dp 16).

EXPERIMENT 3
STUDY OF BINDING TO ENDOTHELIAL CELLS OF THE HUMAN UMBILICAL VEIN, MEASURED BY A COMPETITION EXPERIMENT WITH $^{125}$I-LABELLED HEPARIN

| Substance tested | Molecular weight | $OSO_3^-/COO^-$ | Anticoagulant activity in vitro (U/mg) | | Affinity for endothelial cells $I_{50}$ ($\mu$M) |
|---|---|---|---|---|---|
| | | | APTT | Anti-Xa | |
| Heparin standard | 15.000 | 2.16 | 144 | 165 | 0.17 |
| Heparin sursulfated IC 84 1345 | (6.000–25.000) | 3.01 | 60 | 35 | 0.025 |
| IC 83 1422 CY 216 | 4.500 | 2.1 | 26 | 224 | 15 |
| IC 84 1546 CY 216 | (1.800–3.000) | 2.5 | 22 | 30 | 0.15 |

-continued

| Substance tested | Molecular weight | $OSO_3^-/COO^-$ | Anticoagulant activity in vitro (U/mg) APTT | Anti-Xa | Affinity for endothelial cells $I_{50}$ ($\mu M$) |
|---|---|---|---|---|---|
| sursulfated | | | | | |
| IC 79 797 CY 216 | 2.500 (1.500–8.000) | 2.1 | 12 | 250 | >100 |
| IC 83 1434 Fraction 8000 | 8.000 | 2.1 | 12 | 250 | 0.52 |
| IC 84 1552 dp 16 | 5.000 | 2.04 | 10 | 224 | >100 |
| IC 85 1601 dp 16 sursulfated | | 3.35 | 15 | 23 | 0.32 |
| IC 85 1473 dp 12 | 3.800 | 2.26 | 6 | 200 | >100 |
| IC 85 1600 dp 12 sursulfated | | 2.91 | 5 | 30 | 8.0 |
| IC 84 1475 dp 8 | 2.500 | 2.41 | 3 | 143 | >100 |
| IC 85 1599 dp 8 sursulfated | | 2.95 | 4 | 39 | 20 |

In a general manner, sursulfation increases binding to the endothelial cells of the human umbilical vein.

However, the short chains have only very low affinity for endothelial cells.

EXPERIMENT 4

ACTION ON THE COMPLEMENT SYSTEM

In this model system, the capacity to inhibit the formation of the $C_3$ convertase of the alternate complement activation pathway in an in vitro system of purified proteins was measured.

| SUBSTANCE TESTED | IC 50 $\mu g/ml$ |
|---|---|
| Heparin standard | 0.5 |
| IC 84 1545 Heparin sursulfated | 0.530 |
| IC 84 1444 Heparin N-desulfated N-acetylated | 1–1.65 |
| IC 86 1746 Heparin N-desulfated N-acetylated sursulfated | 0.35 |
| IC 84 1552 dp 16 | 0.75 |
| IC 85 1601 dp 16 sursulfated | 0.30 |
| IC 84 1473 dp 12 | 1.1 |
| IC 85 1600 dp 12 sursulfated | 0.40 |
| IC 84 1475 dp 8 | 3 |
| IC 85 1599 dp 8 sursulfated | 1.1 |
| IC 84 1476 dp 6 | 7 |
| IC 85 1598 dp 6 sursulfated | 1.75 |
| IC 84 1477 dp 4 | 30 |
| IC 85 1597 dp 4 sursulfated | 7 |

The results show that sursulfation does not alter the activity of heparin.

In contrast, the inhibitory activity of N-desulfated, N-acetylated heparin and that of the fragments dp 4 to 16 is increased by sursulfation.

EXPERIMENT 5

INHIBITORY ACTIVITY OF LOW MOLECULAR WEIGHT FRAGMENTS DERIVED FROM CY 222 TOWARDS ELASTASE AND CATHEPSIN G

| SUBSTANCE TESTED | % INHIBITION Elastase | Cathepsin G |
|---|---|---|
| Heparin standard | 100% | — |
| IC 84 1545 Heparin sursulfated | 100% | — |
| IC 84 1555 dp 22 | 91% | 53% |
| IC 84 1554 dp 20 | 92% | 54% |
| IC 84 1552 dp 16 | 82% | 49% |
| IC 85 1601 dp 16 sursulfated | 100% | 60% |
| IC 84 1473 dp 12 | 92% | 46% |
| IC 85 1600 dp 12 sursulfated | 97% | 51% |
| IC 84 1475 dp 8 | 53% | 34% |
| IC 85 1599 dp 8 sursulfated | 95% | 53% |
| IC 84 1476 dp 6 | 38% | 8% |
| IC 85 1598 dp 6 sursulfated | 91% | 43% |
| IC 84 1477 dp 4 | 28% | 7% |
| IC 85 1597 dp 4 sursulfated | 93% | |

It can be seen that, for a given molecular size, the inhibitory power is increased considerably by sursulfation.

This phenomenon is particularly evident with the fragments of lowest molecular weight (dp 4, dp 6).

In conclusion, it can be seen that, depending on the experimental model used (action on blood coagulation or action on other biological systems), sursulfation does not produce the same effects.

It can be observed in particular in the case of very low molecular weight fragments (4 to 8 residues) that inhibitory activity towards the complement system and elastase is markedly increased by sursulfation, whereas activity towards coagulation is only slightly changed, if at all, and remains Very low.

The in vivo effect of the substances of the invention was tested in the following two experimental models:
a model which employs rats sensitized to dextran in the following experimental design:

Rats are sensitized to dextran by the injection of 10 to 50 mg of dextran in suspension in incomplete Freund's adjuvant.

The sensitization is Carried out in 3 series of subcutaneous injections of dextran, the dose to be administered being given in 10 injections made each time at different parts of the body of the animal. The series of injection were performed at intervals of 3 weeks.

The sensitized animals are divided into 2 groups which received either dextran alone or dextran plus the test substances. A third group of animals received nothing and thus served as controls;

The test substances are injected either intravenously a ¼ hour before the injection of the dextran, or subcutaneously 1 to 2 hours before the injection of the dextran, at doses ranging from 1 to 10 mg per kilo body weight.

Assessment of the results of treatment is made on samples of plasma taken from the treated animals (0.5 ml) at 5 mn, 30 mn and 4 h after the injection.

The criteria on which the assessment of the results are based are the following:

(a) measurement of the lysis of sheep erythrocytes coated with rabbit anti-sheep erythrocyte antibodies (CH 50 test).

Serial dilutions are tested and the results are expressed in percentage of the lysis of erythrocytes by the plasma at each of the dilutions. Lysis is estimated by the amount of hemoglobin released, the latter being determined by optical density measurement. (Kabat, E. A. and Meyer, in Experimental Immunochemistry, 2nd edition, Charles C. Thomas, editor, Springfield, Ill. USA (1967), p.149 - Kazatchkine, N. D., Hauptmann, G. and Nydegger, U., in Technique du Complement, edition INSERM, paris, (1985), p. 22-30).

(b) hemagglutination test

This test makes use of sheep erythrocytes coated with dextran and the precipitation of these erythrocytes by anti-dextran antibodies present in the plasma of the animal is measured in microtitration plates, the results being expressed in terms of the greatest dilution of plasma which still leads to precipitation.

a model in which arthritis is experimentally induced in the rat by the administration of complete Freund's adjuvant according to the following procedure :

Male Lewis rats (160-200 g) received an injection of complete Freund's adjuvant (CFA 0.1 ml of Mycobacterium butyricum and a suspension of paraffin oil in water 6 mg/ml), the mixture being injected into the longitudinal arch of the rear left foot.

3 groups of animals are used. One received CFA only, another CFA plus the test substance and the third group received no treatment and thus served as controls.

The test substances are administered intravenously or subcutaneously at doses ranging from 1 to 10 mg/kg per day for 19 days following the injection of CFA.

The results are assessed, on the one hand, by measurement of the volume of the rear right foot which was not injected (secondary lesion), and, on the other, by the determination of the arthritic index. (Perper, R. J., Alvarez, B., Colombo, C., Schroder, H. (1971), proc. Soc. Exp. Biol. Med., 137. p. 506-512 Bartlett, R. R., Schleyerbach, R., (1985), Int. J. Immunopharmac. Vol. 7, No. 1, p. 7-18).

An initial study of the sursulfated octasaccharide of Example 5 showed a positive effect in these two model systems.

In addition, the GAGs of the invention bearing a variable number of charged groups are advantageously devoid of toxic effects.

The $LD_{50}$ was studied by intravenous administration to female "swiss CF" mice, weighing about 20 g, and divided into groups of 5 animals. Injection volume : 0.5 ml ; final doses 62.5 mg/kg, 125 mg/kg, 250 mg/kg, 500 mg/kg, 1,000 mg/kg.

Under the defined experimental conditions, the $LD_{50}$ is higher than 100 mg for 2 substances tested, IC 86 1716 of example 2 and sursulfated decasaccharide IC 86 1746 of example 5.

None of the animals died as a result of the injection or during the 7 days of observation which followed.

Thus, these substances are particularly valuable for the preparation of medicines.

The substances with a dp higher than 12 which have preserved anticoagulant and antithrombotic activity can be used for the prevention and treatment of thromboses. The substances with a lower dp, in particular, those with a dp of 8 or lower are particularly valuable for the treatment of disorders of the vascular wall, of tissue ageing and degenerative symptoms, in particular, disorders arising from certain defects in the immune response such as glomerulonephritis, rheumatoid arthritis and certain types of delayed hypersensitivity giving rise to allergic symptoms.

They may be used in states of shock, in particular, in cases of severe burns.

The pharmaceutical preparations according to the invention are characterized in that they contain an efficacious amount of the GAGs defined above in combination with pharmaceutical excipients. In an advantageous manner, these pharmaceutical preparations are devoid of pyrogens when they are intended for parenteral administration.

Preferred compositions include a pharmaceutical vehicle suitable suitable for oral administration. Appropriate forms of administration of the invention advantageously include gastro-resistant capsules, tablets or lozenges, and pills, or are presented in the form of liposomes.

Other pharmaceutical compositions include these GAGs in combination with excipients suitable for rectal administration. Suppositories provide appropriate forms of administration.

In other pharmaceutical compositions the GAGs are presented in the form of aerosols or ointments.

The invention also relates to injectable pharmaceutical compositions, sterile or sterilizable, for intravenous, intramuscular and subcutaneous administration.

These solutions advantageously contain from 1 to 200 mg/ml of GAGs, preferably from 20 to 150 mg/ml when these solutions are intended for subcutaneous injection. They may contain, for example, from 30 to 100 mg/ml, in particular from 40 to 50 mg/ml of GAGs when they are intended for intravenous injection or perfusion.

Advantageously, such pharmaceutical preparations are available in disposable syringes, ready to use.

The pharmaceutical compositions of the invention are particularly suited to the control (preventive or curative) of some of the steps in blood coagulation in man and animals, particularly in cases where the patient is subject to risks of hypercoagulability resulting, in particular, from surgical operations, atheromatous processes, development of tumors and disorders of coagulation induced by bacteria or enzymes.

Some compositions are capable of modulating the action of complement, in particular, in syndromes of an inflammatory nature, such as those implicated in rheumatism. It is in fact known that some of the disorders observed may be due, at least in part, to the presence of large amounts of antigen-antibody complexes in the joints and in which complement plays a role.

Other compositions are efficacious for combatting ageing of tissues in general or degenerative symptoms such as alopecias.

In order to illustrate the invention, an example of the dosage used in man will be given : the dose consists of the administration of about 1 mg to 1.5 g/24 hours, preferably from 5 mg to 500 mg/24 hours, for example about 200 mg/24 hours intravenously, as discontinuous administrations or administration at regular intervals or orally. Obviously, these doses can be adjusted to the needs of each patient as a function of the results of blood analyses carried out beforehand, the nature of the disease he is suffering from and the general state of his health.

The invention also relates to the application of the GAGs according to the invention to the preparation of useful laboratory biological reagents, in particular as references for use in the comparative study of other substances tested for their inhibitory activity towards proteases.

Other properties and advantages of the invention will appear in the examples which follow relating to the synthesis of substances according to the invention and by making reference to FIGS. 1 to 5.

Figure 2:
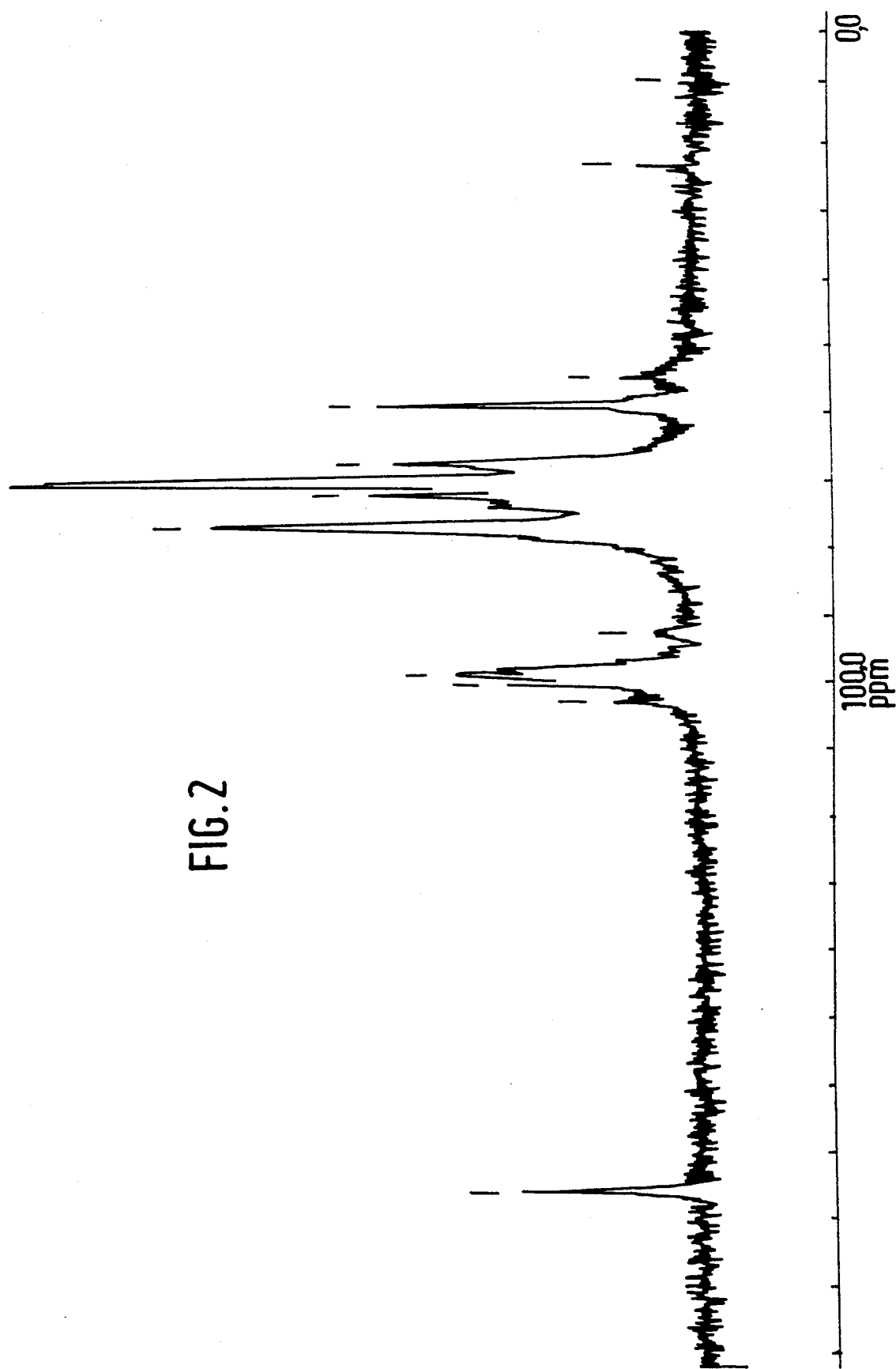
Figure 3:
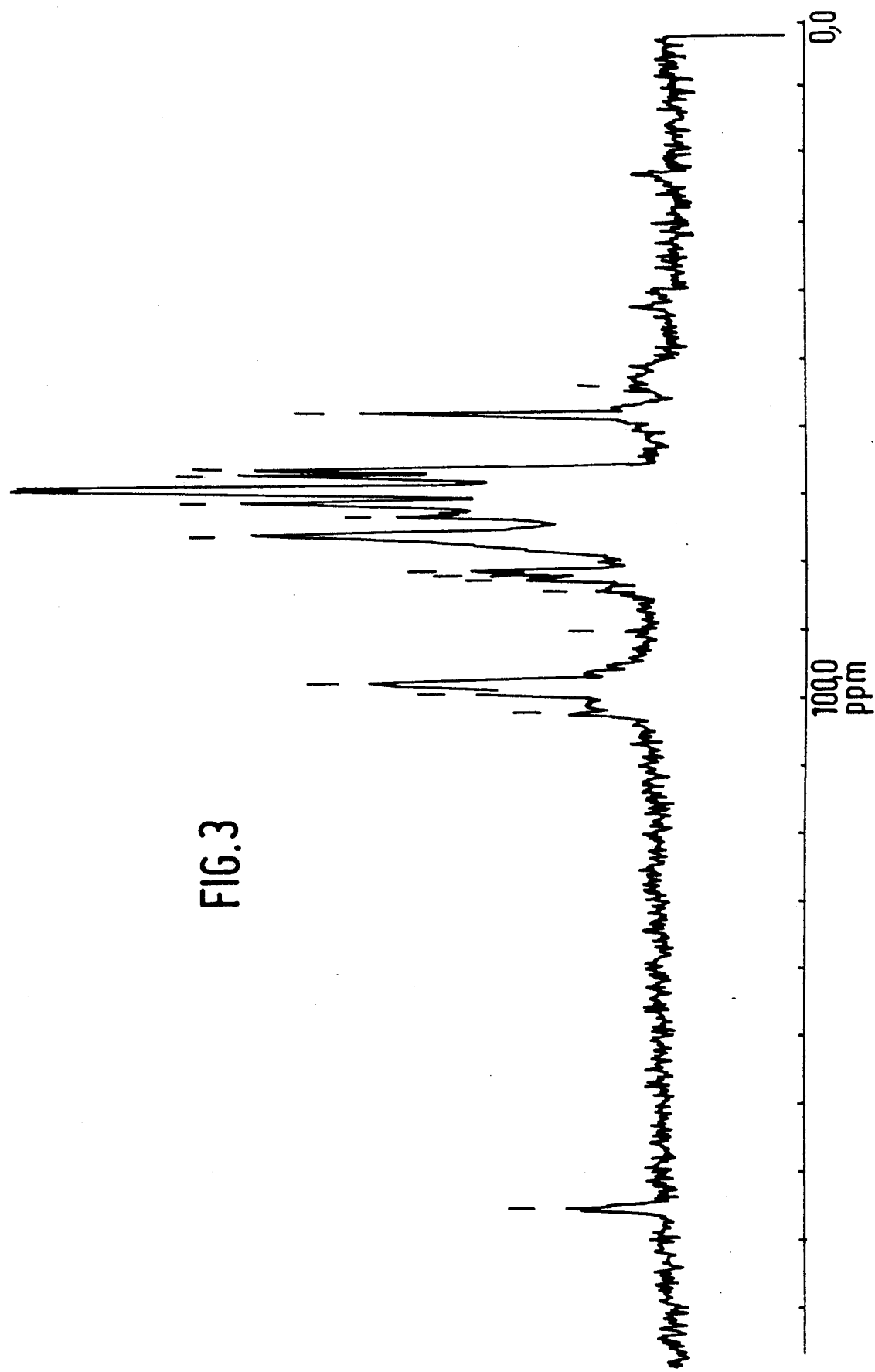
Figure 4:
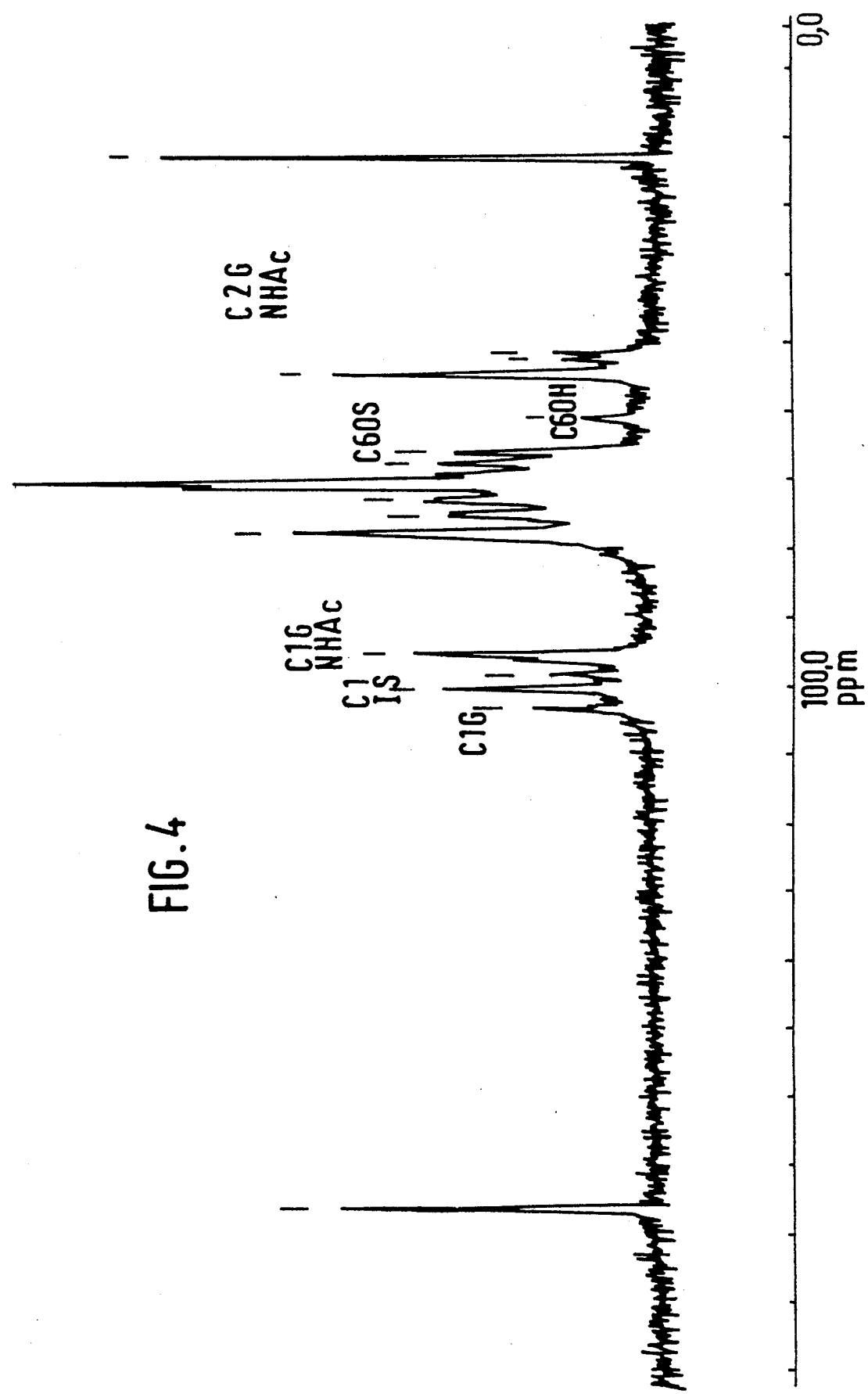
Figure 5:
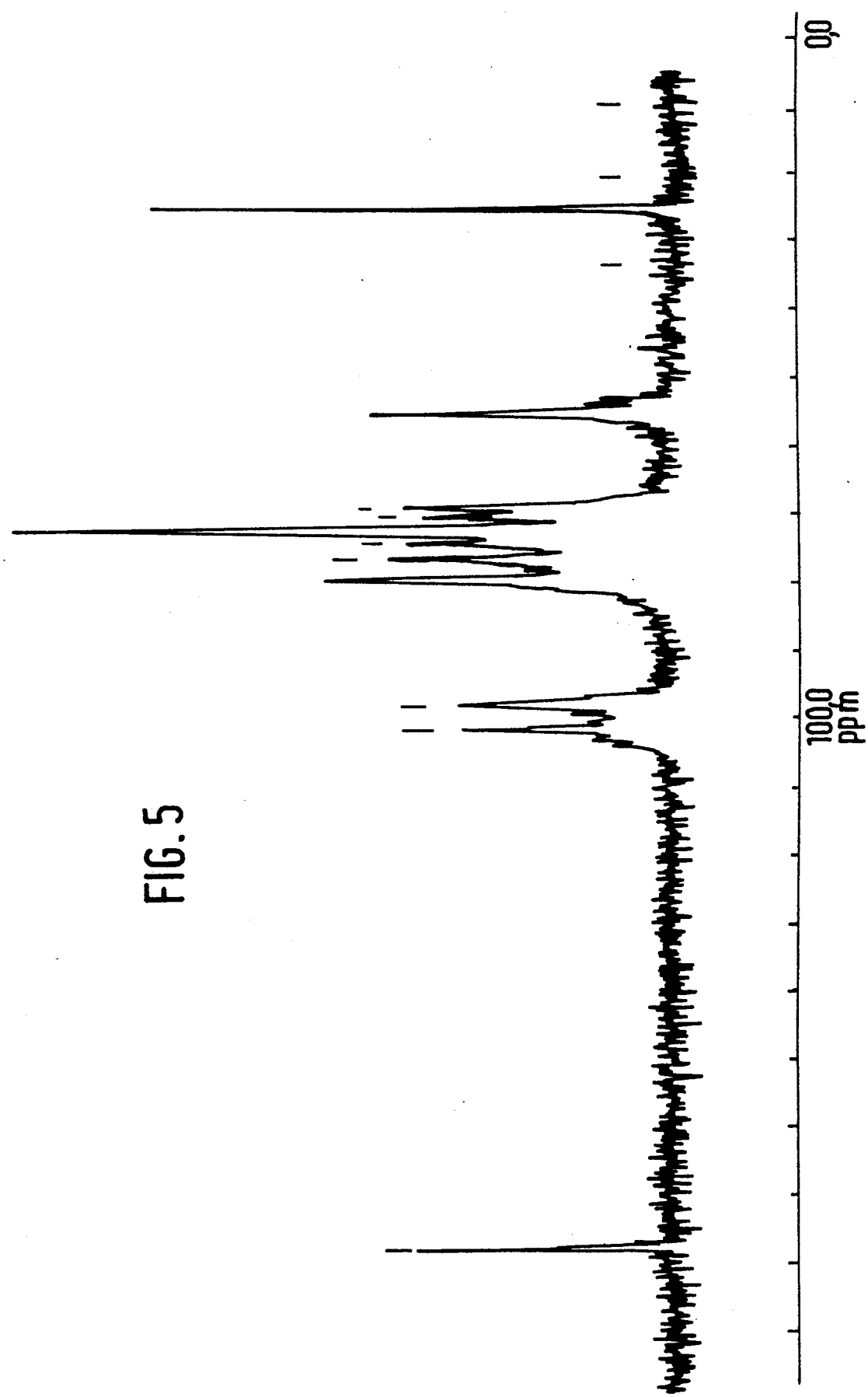

FIGS. 1 and 2 present respectively NMR spectra of heparin and heparin sulfated according to the invention, FIG. 3 presents the NMR spectrum of a low molecular weight heparin sulfated according to the invention, FIGS. 4 and 5 present the NMR spectra of an N-acetylated heparin and the same substance sulfated according to the invention, resp.

EXAMPLE 1

Preparation of heparin with an altered sulfation pattern (IC 84 1545).

Triethylammonium (TEA) heparinate is first prepared and then this salt is subjected to sulfation.

a. Preparation of triethylammonium (TEA) heparinate 1 g of sodium heparinate dissolved in 50 ml of water is converted into the free acid by means of an ion exchange resin (Dowex 50, $H^+$). After neutralization by triethylamine and concentration to dryness 1.3 g of the TEA salt are obtained.

b. Sulfation

To 0.97 g of the above salt, dissolved in dimethylformamide (DMF), the sulfation complex TMA/SO$_3$ 6.8 g is added. After 24 hours at 50° C., the reaction mixture is diluted and passed over a column of Sephadex G-25 to give the product. The sodium salt is obtained by neutralization of the acid form eluted from an ion exchange resin Dowex 50 $H^+$. After lyophilisation, 774 mg of product are obtained.

c. Characterization

The heparin obtained possesses a degree of sulfation (sulfate/carboxylate $SO_3^-/COO^-$) of 3.01 compared with 2.16 for the starting material.

If the reaction time is limited to one hour, the ratio $SO_3^-/COO^- = 2.70$.

In the presence of 0.68 g of sulfating complex and a reaction time of one hour, a $SO_3^-/COO^-$ ratio of 2.40 is obtained.

The NMR spectra of heparin and sursulfated heparin are presented in FIGS. 1 and 2.

The NMR spectra of heparin and hypersulfated heparin are presented in FIGS. 1 and 2. In particular, the disappearance of the CH$_2$OH signal at 62.4 ppm is to be noted, a consequence of its conversion to CH$_2$OSO$_3$. Important changes are also observed in the region of the anomeric carbon atoms (at about 100 ppm).

EXAMPLE 1A

Variant for the Preparation of heparin with an altered sulfation pattern

The same procedure is used as in Example 1, with the difference that chlorosulfonic acid in pyridine is used as sulfating agent instead of the TAM/SO$_3$ complex. In the sulfation reaction, 0.97 g of the TEA salt, dissolved in pyridine, are used and chlorosulfonic acid (1 g) is added.

After 24 hours at 0° C., the reaction mixture is diluted and worked up as in Example 1.

A heparin is obtained with the same properties as those given above.

EXAMPLE 2

Preparation of sursulfated N-acetylated heparin (IC 86 1746)

a. Preparation of the triethylamine salt of N-acetylated heparin

Heparin is N-desulfated by the standard technique (Inoue, S. and Nagasawa, K., Carbohyd. Res., 46 (1976), 87–95), and then acetylated with acetic anhydride in aqueous base. The TEA salt is then prepared in a manner identical with that described in Example 1.a.

b. Sulfation

The TEA salt obtained from 1 gram of N-acetylated heparin is dissolved in DMF (25 ml), then heated at 100° C. in the presence of TMA/SO$_3$ (0.84 g) overnight. The sulfated product is recovered after gel filtration on Sephadex G 25. It is converted into the sodium salt via the free acid. After lyophilisation, 1.14 g of the slightly beige sodium salt is obtained (IC 86 1716). FIGS. 4 and 5 show the NMR spectra of N-acetylated heparin and the corresponding sursulfated derivative.

EXAMPLE 3

Preparation of sursulfated N-acetylated heparin of low molecular weight a. Preparation of the tetrabutylammonium (TBA) salt of N-acetylated heparin of low molecular weight The procedure described in Example 2 is applied to a low molecular weight heparin and tetrabutylammonium hydroxide is used as base.

b. Sulfation

The salt obtained (1 g) is sulfated by the pyridine/SO$_3$ complex (1 g) in pyridine (10 ml at ambient temperature for 24 hours). After gel filtration and conversion to the sodium salt, 0.5 g of the sodium salt of the low molecular weight N-acetylated heparin is obtained.

c. Characterization 35 The above procedure applied, for example, to substance CY 216 as obtained according to Example 1 of the main patent 2 440 376 cited above (average dp of about 14) leads to a sursulfated product having an $SO_3^-/COO^-$ ratio of 2.85, compared with 2.12 for the starting material.

EXAMPLE 4

Preparation of sursulfated heparin of low molecular weight a. Preparation of the tetrabutylammonium salt of low molecular weight heparin The substance CY 216 is dissolved in water (10 g in 0.5 l) and converted into the acid form by passage through a column of Dowex 50 WX4 in the $H^+$ form. After neutralization, the tetrabutylammonium heparinate obtained is lyophilised to give 19.34 g.

b. Sulfation 1 g of the above salt is dissolved in anhydrous pyridine and the sulfation complex (pyridine/SO$_3$) is added.

Three different experiments using different amounts of the complex were performed. After the reaction has been allowed to proceed for 24 hours at ambient temperature, the mixture is poured into a solution of sodium hydroxide (2 g) in 95 % ethanol. The precipitate formed is filtered off, dissolved in water, chromatographed on Sephadex G 25 and lyophilised to give the sodium salt.

c. Characterization

The degree of sulfation of the product can be varied by varying the amount of sulfation complex. Thus, utilisation of 0.16 g, 0.32 g and 0.48 g of the sulfation complex gives rise, respectively, to degrees of sulfation of 2.21, 2.75 and 3.41.

The NMR spectrum of sursulfated CY 216 is presented in FIG. 3.

The C-1 signal of the anhydromannitol (53.6 ppm) has disappeared ($CH_2OH \rightarrow CH_2OSO_3^-$) and the other signals of mannitol (78.86 ppm region) are modified. The same is true for the signals of the anomeric atoms at about 100 ppm.

EXAMPLE 5

Preparation of oligosaccharides with a homogeneous degree of polymerization and an altered sulfation pattern a. Preparation of oligosaccharides They are obtained by fractionation by means of gel filtration of a mixture resulting from the depolymerisation of heparin under controlled conditions by heparinase or nitrous acid. Depolymerisation procedures using nitrous acid are described, in particular, in the second certificate of addition 2 478 646 of the 20.03.1980 and in the application FR 2 503 714 of the 10.04.1981, depolymerisation by means of heparinase is described in application EP 0027089. These patents and patent applications, filed in the name of the applicant, are mentioned above. The depolymerisation mixture (1 g) is placed on top of a column of Sephadex G 50 (2.5×300 cm) and eluted with 0.2 M sodium chloride solution. The fractions corresponding to well defined oligosaccharides (di-, tetra-, hexa-, octa- . . . up to icosasaccharides) are pooled, concentrated and desalted. The products are isolated by lyophilisation.

b. Preparation of the tetrabutylammonium salts

They are prepared according to the method described in 4a. The salts of tetra-, hexa-, octa-, dodeca- and hexadecasaccharides were obtained, each group of products having an unsaturated uronic acid residue at the non-reducing terminal.

c. Sulfation of the oligosaccharides

The tetrabutylammonium salt of the oligosaccharide to be sulfated is dissolved in DMF (250 mg/5ml), and then the sulfation complex (trimethylamine/$SO_3$; 250 mg) is added. The reaction mixture is maintained at 50° C. for 24 hours and then diluted with water (5 ml). The sulfated oligosaccharide is obtained by lyophilisation after the reaction mixture has been chromatographed on Sephadex G 25.

| Oligosaccharide | dp | $SO_3^-/COO^-$ |
|---|---|---|
| Disaccharide | 2 | 3 |
| Disaccharide sursulfated | 2 | 4.1 |
| Tetrasaccharide (IC 41477) | 4 | 2.46 |
| Tetrasaccharide sursulfated (IC 85 1597) | 4 | 3.20 |
| Hexasaccharide (IC 84 1476) | 6 | 2.22 |
| Hexasaccharide sursulfated (IC 85 1598) | 6 | 3.00 |
| Octasaccharide (IC 84 1475) | 8 | 2.43 |
| Octasaccharide sursulfated | 8 | 3.08 |
| Decasaccharide (IC 86 1746) | 10 | 1.95 |
| Decasaccharide sursulfated | 10 | 2.76 |

EXAMPLE 6

Preparation of sursulfated dermatan sulfate (IC 85 1610)

a. Preparation of the tetrabutylammonium salt 25 mg of dermatan sulfate are converted to the acid form (cation exchange resin), then neutralized with tetrabutylammonium hydroxide. 46 mg of the salt are obtained on lyophilisation.

b. Sursulfation of dermatan sulfate

The salt obtained in the preceding experiment (15 mg) is hypersulfated in DMF (1 ml) by the addition of the trimethylamine/$SO_3$ complex (15 mg). The product is obtained by dilution with water, gel filtration on Sephadex G 25 and, finally, by exchange of the organic cation for sodium by means of an ion exchange resin.

EXAMPLE 7

Preparation of sursulfated heparan sulfate a. Preparation of the triethylamine salt The starting material (0.8 g) is dissolved in water, converted to the free acid form and neutralized with triethylamine. After lyophilisation, 0.91 g of the triethylamine salt is obtained.

b. Sursulfation

The above salt (0.24 g) is in DMF (8 ml) by warming. After addition of the sulfation complex (TMA/$SO_3$; 1.68 g), the reaction mixture is maintained at 50° C. for 24 hours. After gel filtration and conversion to the sodium salt, 238 mg of the sursulfated heparin is obtained.

EXAMPLE 8

Preparation of heparin sursulfated at positions 2 and 3 of the constituent monosaccharides This example provides an illustration of the flexibility of the procedure. N,O-desulfated heparin is first prepared according to the technique of NAGASAwA et al., Carbohyd. Res. 58, (1977), 47-55.

The heparin thus obtained is then selectively N-resulfated by means of the pyridine/$SO_3$ complex at basic pH. It is finally converted into the tetrabutylammonium salt Via the intermediary of the free acid which latter is neutralized with tetrabutylammonium hydroxide. The salt obtained is dried at 50° C. in a vacuum for 24 hours.

The tetrabutylammonium salt (0.92 g) is then dissolved in anhydrous pyridine (10 ml). Acetic anhydride (0.1 ml) is added and the reaction mixture is left overnight at ambient temperature. After addition of the sulfation complex (pyridine/$SO_3$; 0.72 g), the reaction mixture is heated to 100° C. for 4 hours. After being cooled, it is poured slowly into ethanol (100 ml) containing sodium hydroxide (2 g). After being left to stand overnight at 4° C., the precipitate obtained is dried, dissolved in water and chromatographed on Sephadex G 25. After lyophilisation, 0.67 g of a powder are obtained ; analysis shows that about 60 % of the primary OH groups are free.

EXAMPLE 9

Preparation of sursulfated N-acetylated hexasaccharides

The hexasaccharide fraction described in Example 5a is converted into its pyridine salt, then N-desulfated by heating for 90 minutes at 50° C. in a mixture of DMSO/H$_2$O (95/5 v/v). After addition of sodium hydroxide, the reaction mixture is chromatographed on a column of Sephadex G 25. After lyophilisation, the product is recovered as the free amine. It is N-acetylated according to the standard procedure with acetic anhydride in base.

The N-acetyl derivative (0.5 g) is converted into its tetrabutylammonium salt. This is then dissolved in DMF (10 ml) and sulfated at 100° C. for 4 hours in the presence of the trimethylamine/SO$_3$ complex (0.5 g). After being cooled, the reaction mixture is poured slowly into a 0.5 M solution of sodium hydroxide in ethanol (90 ml). After centrifugation, the pellet is recovered. It is dissolved in water and lyophilised to give 0.61 g of the hypersulfated N-acetylated hexasaccharides as their sodium salts.

EXAMPLE 10

Preparation of sursulfated fragments of dermatan sulfate

Fragments of dermatan sulfate are obtained by the standard method (periodate oxidation, followed by controlled acid hydrolysis : TOLLEFSEN, Nouvelle Revue Francaise d'Hematologie 26, (1984), 233–237 or by hydrazino)ysis, followed by degradation with nitrous acid, or by the method described below).

Dermatan sulfate (Sigma), 50 mg, is dissolved in a 0.5 M solution of hydrochloric acid (2 ml). After being heated for 5 minutes at 100° C., the mixture is cooled. An aqueous solution of sodium nitrite (2.5 % ; 1 ml) is then added. After 1 minute, sodium hydroxide is added to neutralize the acid. The mixture is desalted on a column of Sephadex G 25.

After lyophilisation, the product obtained is converted into its triethylamine salt and then sulfated at 100° C. in DMF (5 ml) in the presence of the trimethylamine/SO$_3$ complex (50 mg). After 4 hours, the mixture is cooled, placed on top of a column of Sephadex G 50 and eluted with water. The sodium salt is obtained via the free acid form which is subsequently neutralized with sodium hydroxide. This neutralization, monitored by conductivity, indicates a sulfate/carboxylate ratio of 2.4.

The time of hydrolysis or the temperature or the molarity of the acid may be modified to allow the preparation of fragments of different size. The degree of sulfation can also be modulated by changing the conditions of the sulfation reaction.

This reaction sequence can be applied under the same conditions to the chondroitin sulfates.

We claim:

1. A process for the sulfation of glycosaminoglycans, which process comprises
    (a) first, converting the glycosaminoglycans into amine salts, which salts are soluble in a dipolar aprotic solvent, and which salts allow the glycosaminoglycans to be treated with a sulfating agent without altering the degree of polymerization of the glycosaminoglycans, then
    (b) dissolving the salts in the dipolar aprotic solvent, and
    (c) treating the solution formed with the sulfating agent.

2. A process according to claim wherein the glycosaminoglycan is comprised of alternating residues of D-glucosamine and a uronic acid selected from the group consisting of L-iduronic acid and D-glucuronic acid.

3. A process according to claim 2, wherein the glycosaminoglycan is selected from the group consisting of heparin, heparan sulfate, and fractions and fragments of heparin and heparan sulfate.

4. A process according to claim 2, wherein the glycosaminoglycan is a glycosaminoglycan of low molecular weight comprising a mixture of chains, or chains homogeneous with respect to their degree of polymerisation, having a number of sugar residues less than that of a heparin or heparan sulfate.

5. A process according to claim 4, wherein the number of sugar residues ranges from 2 to 30.

6. A process according to claim 4, wherein the staring glycosaminoglycan is selected from the group consisting of
    (a) mucopolysaccharides obtained from heparin by alcoholic extraction, and comprising a mixture of chains of molecular weights of about 2,000 to 8,000, and possessing ratios of Yin-Wessler/USP titers of at least 2;
    (b) mucopolysaccharides obtained by limited depolymerisation of heparin by nitrous acid, and comprising a mixture of chains of molecular weights of about 2,000 to 8,000 and possessing ratios of Yin-Wessler/USP titers of at least 2, and being terminated by residues with a 2,5-anhydromanno structure;
    (c) mucopolysaccharides composed essentially of chains
        (1) of average molecular weight of from 3,000 to 6,000;
        (2) possessing a Yin-Wessler (YW)/USP ratio of less than 10; and
        (3) terminated by residues of a 2,5-anhydromanno structure;
    (d) oligosaccharides composed of maximally 8 sugar residues, having a high Yin-Wessler titer and a low USP titer, having a high affinity of Antithrombin-III (AT-III) these oligosaccharides being terminated by a residue with a 2,5-anhydromanno structure or bearing a residue at the beginning of the chain corresponding to an unsaturated uronic acid residue as obtained by heparinase depolymerization;
    (e) homogeneous hexasaccharide compounds corresponding the formula below:

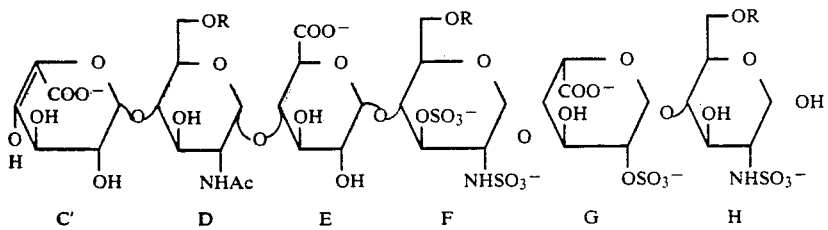

wherein R is selected from the group consisting of H and $SO_3^-$;

(f) oligo- or polysaccharides, homogeneous with respect to degree of polymerisation, obtained by filtration or by chromatography employing an ionic strength gradient of glycosaminoglycans or their fragments;

(g) glycosaminoglycans obtained by reacting periodate with heparin, and treating the resulting product with base;

(h) glycosaminoglycans obtained by depolymerising heparin with heparinase or nitrous acid, separating the fractions possessing the sequence which binds to AT-III and gel filtering these fractions to obtain a glycosaminoglycan fragment;

(i) glycosaminoglycans obtained by depolymerising heparin with heparinase or nitrous acid, but substantially lacking the sequence able specifically to bind to AT-III in procedures which include a step in which heparin or glycosaminoglycans are mixed with AT-III, followed by gel filtration to separate the oligosaccharides of various degrees of polymerisation into homogeneous fragments, and with YW titers approaching zero;

(h) the glycosaminoglycan fractions and fragments of glycosaminoglycans having heparin chain sequences in which at least some of the $-NHSO_3^-$ groups in positions 2 of the glucosamine residues are replaced by $-NH-$acyl or $-NH_2$ groups; and (k) mixtures of glycosaminoglycans comprising total GAG mixtures extracted from animal organs.

7. A process according to claim 6, wherein the mucopolysaccharides defined in subsection (a) have a YW/USP ratio of about 3 to 5 and average molecular weights of 3,000 to 5,500.

8. A process according to claim 7, wherein the mucopolysaccharides are CY 216.

9. A process according to claim 6, wherein the mucopolysaccharides defined in subsection (b) possess a terminal 2,5-anhydromannitol residue.

10. A process according to claim 9, wherein the mucopolysaccharide is CY 222.

11. A process according to claim 6, wherein the mucopolysaccharides defined in subsection (b) possess a terminal 2,5-anhydromannonic residue.

12. A process according to claim 6, wherein the mucopolysaccharides defined in subsection (b) have chains, the majority of which possess molecular weights of about 2,000 to 3,000, with ratios of Yin-Wessler/USP titers of at least 10 and with Yin-Wessler titers of about at least 200 u/mg.

13. A process according to claim 6, wherein the mucopolysaccharides defined in subsection (c) are composed essentially of chains of average molecular weight of about 4,000 to 5,000 and possess a Yin-Wessler/USP ratio of about 6 to 3.

14. A process according to claim 6, wherein the oligosaccharides defined in subsection (d) are octasaccharides of the structure ABCDEFGH, corresponding to the formula:

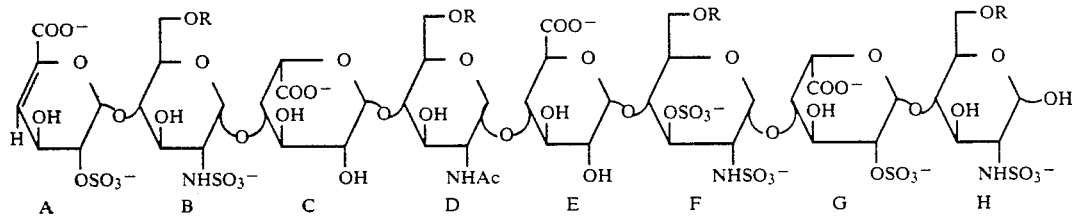

wherein R is selected from the group consisting of H and $SO_3^-$.

15. A process according to claim 6, subsection (g), wherein the base-treated product is further reduced with sodium borohydride.

16. A process according to claim 6, subsection (h), wherein the fragments have a degree of polymerization higher than 12.

17. A process according to claim 6, subsection (h), wherein the fragments have a lower degree of polymerisation and contain 12, 10, 8, 6, 4 and 2 a sugar residues.

18. A process according to claim 1, wherein the glycosaminoglycan is comprised of alternating residues of D-galactosamine and a uronic acid.

19. A process according to claim 18, wherein the glycosaminoglycan is selected from the group consisting of dermatan sulfate, the chrondroitins, the chrondroitin sulfates, hyaluronic acid, and fractions or fragments of the foregoing substances.

20. A process according to claim 18, wherein the glycosaminoglycans are homogeneous with respect to their degree of polymerisation and are obtained by gel filtration of a depolymerised mixture of these glycosaminoglycans.

21. A process according to claim 1, wherein at least one of the primary or secondary $-OH$ groups of the sugar residues of the glycosidic chain of the glycosaminoglycans are protected by protecting groups, which protecting groups can be removed to regenerate $-OH$ groups after other carbon positions of the glycosaminoglycans have been sulfated.

22. A process according to claim 21 further comprising removing the hydroxyl protecting groups after the sulfation step by saponification or hydrogenolysis.

23. A process according to claim 22, wherein the amine component of the salt is selected from a group of amines of the formula —N($R_1$, $R_2$, $R_3$) in which $R_1$, $R_2$ and $R_3$ are a hydrogen atom or an aliphatic chain of from 1 to 10 carbon atoms.

24. A process according to claim 1, wherein the amine component of the salt is selected from the group consisting of triethylamine, tributylamine and a quaternary ammonium salt.

25. A process according to claim 1, wherein the glycosaminoglycan salt is obtained by treating the glycosaminoglycan in its acid form, prepared by chromatography on a cation exchange resin, with an amine to form said salt.

26. A process according to claim 1, wherein the glycosaminoglycan salt is dissolved in an dipolar aprotic solvent selected from the group consisting of dimethylformamide, dimethylsulfoxide and pyridine.

27. A process according to claim 1, wherein the sulfating agent is a complex selected from the group consisting of sulfur trioxide with an organic base, and chlorosulfonic acid in pyridine.

28. A process according to claim 27, wherein the organic base is selected from the group consisting of trimethylamine and pyridine.

29. A process according to claim 27, wherein about 1 to 5 equivalents of complex are used per —OH group of the glycosaminoglycan.

30. A process according to claim 27, 28 or 29, wherein the sulfation reaction is carried out at a temperature of the order of 0° to 100° C. for about 10 to 24 hours.

31. A process according to claim 1, further comprising recovering the sulfated glycosaminoglycan and gel filtering it to obtain a product homogeneous with respect to its degree of polymerisation.

32. The process of claim 1 wherein the reaction is carried out at about ambient temperature.

33. The process of claim 1 wherein the reaction is carried out at about 20° C.

34. Glycosaminoglycans (I) with an altered sulfation pattern, wherein the glycosaminglycans (I) are represented by the following formula I:

R—(XY)$_n$—R'  (I)

in which:
R represents a uronic acid or an unsaturated uronic acid or an OH group;
X represents a glucosamine or a galactosamine moiety in which the carbon atom at position 2 has a substituent which is an $NHSO_3^-$ group, or, in the case of glucosamine and chains of the heparin type, an $NH_2$ or NH-acyl group;
Y represents a uronic acid selected from the group consisting of a D-glucuroic acid and a L-iduronic acid;
n is an integer between 0 and 80;
R' represents a glucosamine or galactosamine moiety in which the carbon atom at position 2 has a substituent which is an $NHSO_3^-$ group, or, in the case of glucosamine and chains of the heparin type, an $NH_2$ or an NH-acyl group, or represents an —O group or a glucosamine residue rearranged to a grouping with a 2,5-anhydromanno structure, or a galactosamine residue rearranged to a grouping with a 2,5 anhydrohexitol structure;
and the position of sulfate groups in the chain of the glycosaminglycans (I) is different from, and the degree of sulfation is greater than that encountered in naturally occurring glycosaminoglycans or depolymerized naturally occurring glycosaminoglycans otherwise having the structure of the glycosaminoglycans (I), said glycosaminoglycans (I) being other than those comprising mixtures of chains (a) with non-modified termini, (b) having a molecular weight less than 9,000, (c) with not more than a minor amount of species greater than 9,000, and their pharmacologically acceptable salts.

35. Glycosaminoglycans according to claim 34, wherein the primary and secondary —OH groups are sulfated.

36. Glycosaminoglycans according to claim 34 which correspond to formula II as follows:

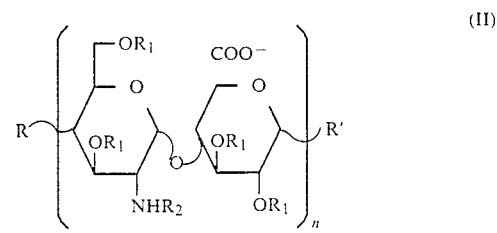

in which
$R_1$ represents H or $SO_3^-$;
$R_2$ represents H, $SO_3^-$ or an acyl group;
R and R' are as given in claim 34; and
n is an integer between zero and eighty.

37. Glycosaminoglycans according to claim 36, wherein $R_2$ represents acetyl.

38. Glycosaminoglycans according to claim 34, wherein the glycosaminoglycans contain one or more galactosamine residues and the linkages between the galactosamine and uronic acid residues are of the 1-4 beta D type and those between the uronic acid and the galactosamine residues are of the 1-3 alpha L or 1-3 beta D type.

39. Glycosaminoglycans according to claim 34, which contain a number of sugar residues less than or equal to 12.

40. Glycosaminoglycans according to claim 39, wherein R represents an unsaturated uronic acid residue.

41. Glycosaminoglycans according to claim 39, wherein R' represents a group with a 2,5-anhydromanno structure.

42. Glycosaminoglycans according to claim 41, wherein R' represents a residue with a 2,5-anhydromannitol structure.

43. Glycosaminoglycans according to claim 39, which comprise glycosaminoglycans homogeneous with respect to their degree of polymerisation, the chains containing four or six sugar residues.

44. Glycosaminoglycans according to claim 31, wherein their chains are homogeneous with respect to their degree of polymerization and contain eight, ten or twelve sugar residues.

45. Glycosaminoglycans according to claim 43, or 44, wherein R and R' both represent an —OH.

46. Glycosaminoglycans according to claim 43, or 44, wherein R and R' respectively are a uronic acid and a glucosamine residue.

47. Glycosaminglycans according to claim 43 or 44, wherein R' represents a residue with the 2,5-anhydromanno structure.

48. Glycosaminoglycans according to claim 43 or 44, wherein R' represents a residue with the 2,5-anhydromannitol structure.

49. Glycosaminoglycans according to claim 34, which contain a mixture of chains in which n is an integer between 3 and 15, and the glycosaminglycans contain a modified terminal sugar residue, which modified residue has a 2,5 anhydromanno structure if it is at the reducing end, and an alpha beta unsaturated structure if it is at the non reducing end.

50. Glycosaminoglycans according to claim 49, which are prepared from starting materials consisting of mucopolysaccharides obtained by limited depolymerisation with nitrous acid, said glycosaminoglycans comprising a mixture of chains with a terminal 2,5-anhydromanno residue, of molecular weights of about 2,000 to 8,000, possessing a ratio of Yin-Wessler/USP titers of at least 10 and a Yin-Wessler titer of a least 200 u/mg.

51. Glycosaminoglycans according to claim 50, wherein the 2,5-anhydromanno residue is a 2,5-anhydromannitol residue.

52. Glycosaminoglycans according to claim 50 or 51, wherein the mucopolysaccharides are composed of a mixture of chains having an average molecular weight of 2000 to 3000.

53. Glycosaminoglycans according to claim 49, which are prepared from starting materials comprising mucopolysaccharides obtained by depolymerisation with nitrous acid, and which comprise a mixture of chains having a terminal 2,5-anhydromanno residue, possessing a ratio of Yin-Wessler/USP titers of about 3 to 6 and average molecular weights of 4,000 to 5,000.

54. Glycosaminoglycans according to claim 53, wherein the 2,5-anhydromanno residue is a 2,5-anhydromannitol residue.

55. Glycosaminoglycans according to claim 54, which contain more than 30 sugar residues.

56. Glycosaminoglycans according to claim 55, which are hypersulfated naturally occurring products, other than hypersulfated heparin.

57. Glycosaminoglycans according to claim 49 or 56, wherein the carbon atom in position 2 of the glucosamine moiety has a substituent which is an-$NH_2$ or-NH-acyl group.

58. Glycosaminoglycans according to claim 57, wherein the carbon atom in position 2 of the glucosamine moiety has a substituent which is —NH-acetyl.

59. A pharmaceutical preparation which comprises as an active ingredient a glycosaminoglycan with a modified sulfation pattern according to claim 34, in combination with a pharmaceutically acceptable carrier.

60. A pharmaceutical preparation, which comprises an efficacious amount of a glycosaminoglycan according to claim 34 in combination with a pharmaceutical vehicle, which preparation is effective in anti-thrombotic, lipid-lowering or fibrinolytic action.

61. A preparation according to claim 60 in the form of a sterile, injectable solution containing from 1 to 100 mg/ml of glycosaminoglycans.

62. A preparation for subcutaneous injection according to claim 61, containing from 20 to 80 mg/ml of glycosaminoglycans.

63. A preparation for intravenous injection or perfusion according to claim 61, containing from 30 to 60 mg/mo of glycosaminoglycans.

64. A preparation according to claim 60 in the form of gastro-resistant capsules, tablets, lozenges, pills or liposomes.

65. Glycosaminoglycans according to claim 34 having a molecular weight greater than 10,000.

66. Glycosaminoglycans according to claim 65 having a molecular weight greater than 11,000.

67. Glycosaminoglycans according to claim 66 which are heparins having a degree of sulfation greater than about 2.5.

68. Glycosaminoglycans according to claim 39 having secondary OH groups sulfated.

69. Glycosaminoglycans according to claim 34 which are heparins having a degree of sulfation greater than about 2.5.

* * * * *

UNITED STATES PATENT AND TRADEMARK OFFICE
CERTIFICATE OF CORRECTION

PATENT NO. : 5,013,724

DATED : May 7, 1991

INVENTOR(S) : Petitou, et al.

It is certified that error appears in the above-identified patent and that said Letters Patent is hereby corrected as shown below:

On title page, after item [22], insert the following:

--[30] Foreign Application Priority Data
　　　Jul. 12, 1985 [DE]　France ................85 107 87--.

Signed and Sealed this

Sixth Day of October, 1992

Attest:

DOUGLAS B. COMER

Attesting Officer　　　Acting Commissioner of Patents and Trademarks

UNITED STATES PATENT AND TRADEMARK OFFICE
CERTIFICATE OF CORRECTION

PATENT NO. : 5,013,724
DATED : May 7, 1991
INVENTOR(S) : Petitou, et al.

It is certified that error appears in the above-identified patent and that said Letters Patent is hereby corrected as shown below:

Column 28, claim 2, line 14 - insert "1," after the word "claim".

Column 29, claim 6, line 46, "(h)" should be "(j)."

Column 29, claim 6, line 49 "positions" should be "position".

Column 31, claim 34, line 66, "--O" should be -- -OH --.

Signed and Sealed this

Ninth Day of November, 1993

Attest:

BRUCE LEHMAN

Attesting Officer    Commissioner of Patents and Trademarks